US 12,064,222 B2

(12) United States Patent
Ono et al.

(10) Patent No.: US 12,064,222 B2
(45) Date of Patent: Aug. 20, 2024

(54) BLOOD PRESSURE MEASUREMENT DEVICE

(71) Applicants: OMRON Corporation, Kyoto (JP); OMRON HEALTHCARE Co., Ltd., Kyoto (JP)

(72) Inventors: Takashi Ono, Kyoto (JP); Yoshihiko Sano, Kyoto (JP); Masaki Harada, Kyoto (JP); Takayuki Matsuoka, Kyoto (JP); Takanori Nishioka, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 679 days.

(21) Appl. No.: 17/304,495

(22) Filed: Jun. 22, 2021

(65) Prior Publication Data
US 2021/0307626 A1    Oct. 7, 2021

Related U.S. Application Data

(63) Continuation of application No. PCT/JP2019/048029, filed on Dec. 9, 2019.

(30) Foreign Application Priority Data

Dec. 27, 2018  (JP) ................. 2018-246102

(51) Int. Cl.
A61B 5/021    (2006.01)
A61B 5/022    (2006.01)

(52) U.S. Cl.
CPC ...... *A61B 5/02141* (2013.01); *A61B 5/02233* (2013.01); *A61B 2560/04* (2013.01)

(58) Field of Classification Search
CPC ....... A61B 5/02; A61B 5/021; A61B 5/02141; A61B 5/022; A61B 5/02233; A61B 5/6824

See application file for complete search history.

(56) References Cited

U.S. PATENT DOCUMENTS

| 7,354,403 B2 * | 4/2008 | Mochizuki ......... A61B 5/02141 600/490 |
| 2006/0058688 A1 * | 3/2006 | Kishimoto ......... A61B 5/02233 600/490 |
| 2006/0135872 A1 * | 6/2006 | Karo .................. A61B 5/02141 600/499 |

FOREIGN PATENT DOCUMENTS

| JP | H11-309119 A | 11/1999 |
| JP | 2005-177321 A | 7/2005 |

(Continued)

OTHER PUBLICATIONS

English Translation of International Preliminary Report on Patentability issued Jul. 1, 2021 in International (PCT) Patent Application No. PCT/JP2019/048029.

Primary Examiner — Eric F Winakur
Assistant Examiner — Abel Seifu Abegaz
(74) Attorney, Agent, or Firm — Wenderoth, Lind & Ponack, L.L.P.

(57) ABSTRACT

Provided is a blood pressure measurement device including a curler including a cover portion that fixes a device body to a hand back side of the wrist, a pressing cuff including a first bag-like structure and a first flow path body which is integrally formed with the first bag-like structure by joining two sheet members forming the first bag-like structure facing the curler and is fluidly connecting a pump and the first bag-like structure, a sensing cuff including a second bag-like structure and a second flow path body which is integrally formed with the second bag-like structure by (Continued)

joining two sheet members forming the second bag-like structure and is including one end disposed on the wrist side of the cover portion, and a tensile cuff including a third bag-like structure.

6 Claims, 26 Drawing Sheets

(56) References Cited

FOREIGN PATENT DOCUMENTS

| | | | |
|---|---|---|---|
| JP | 2017-6488 | A | 1/2017 |
| JP | 2018-102859 | A | 7/2018 |
| JP | 2019-118410 | A | 7/2019 |

* cited by examiner

[FIG. 1]
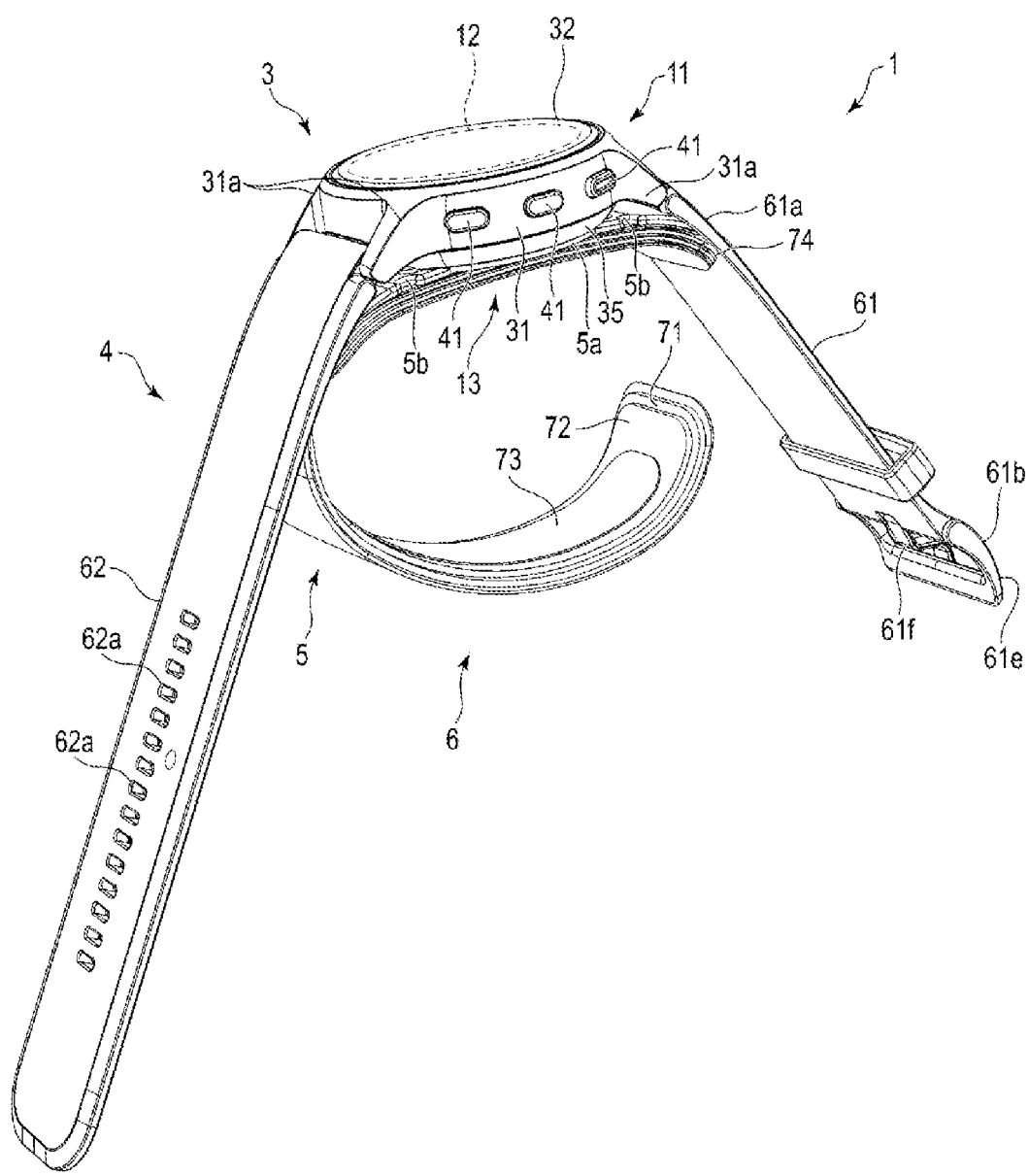

[FIG. 2]
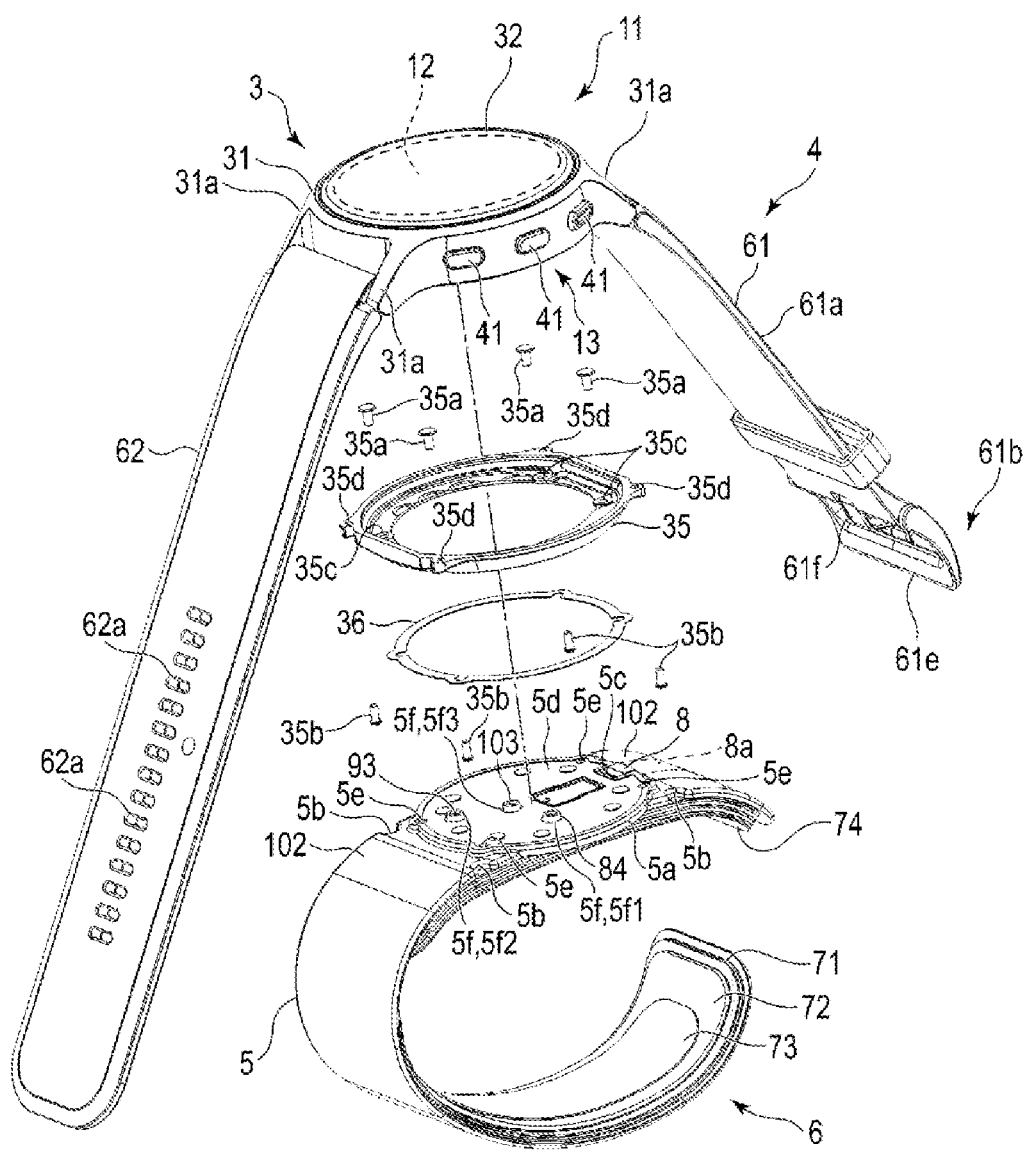

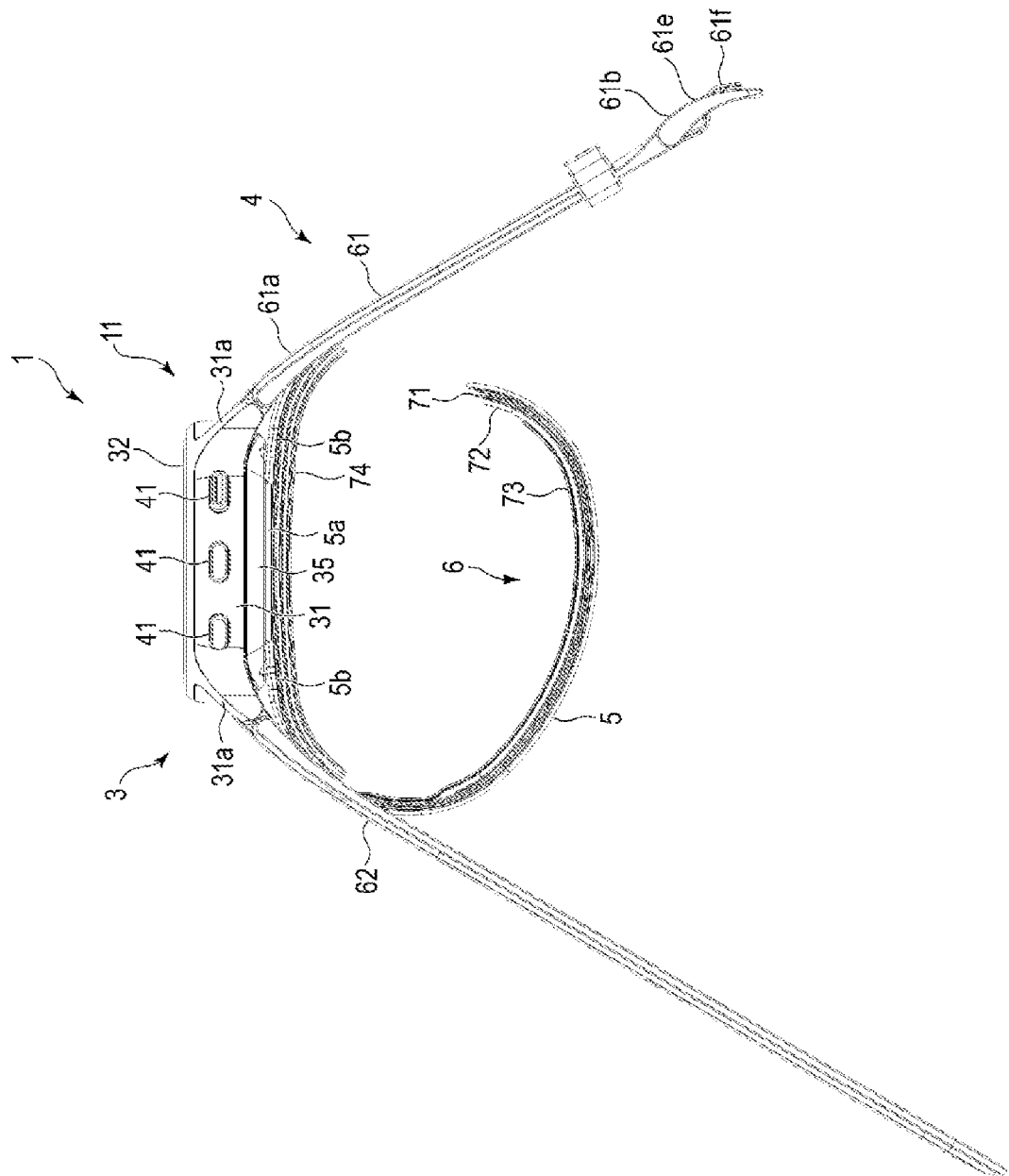
[FIG. 3]

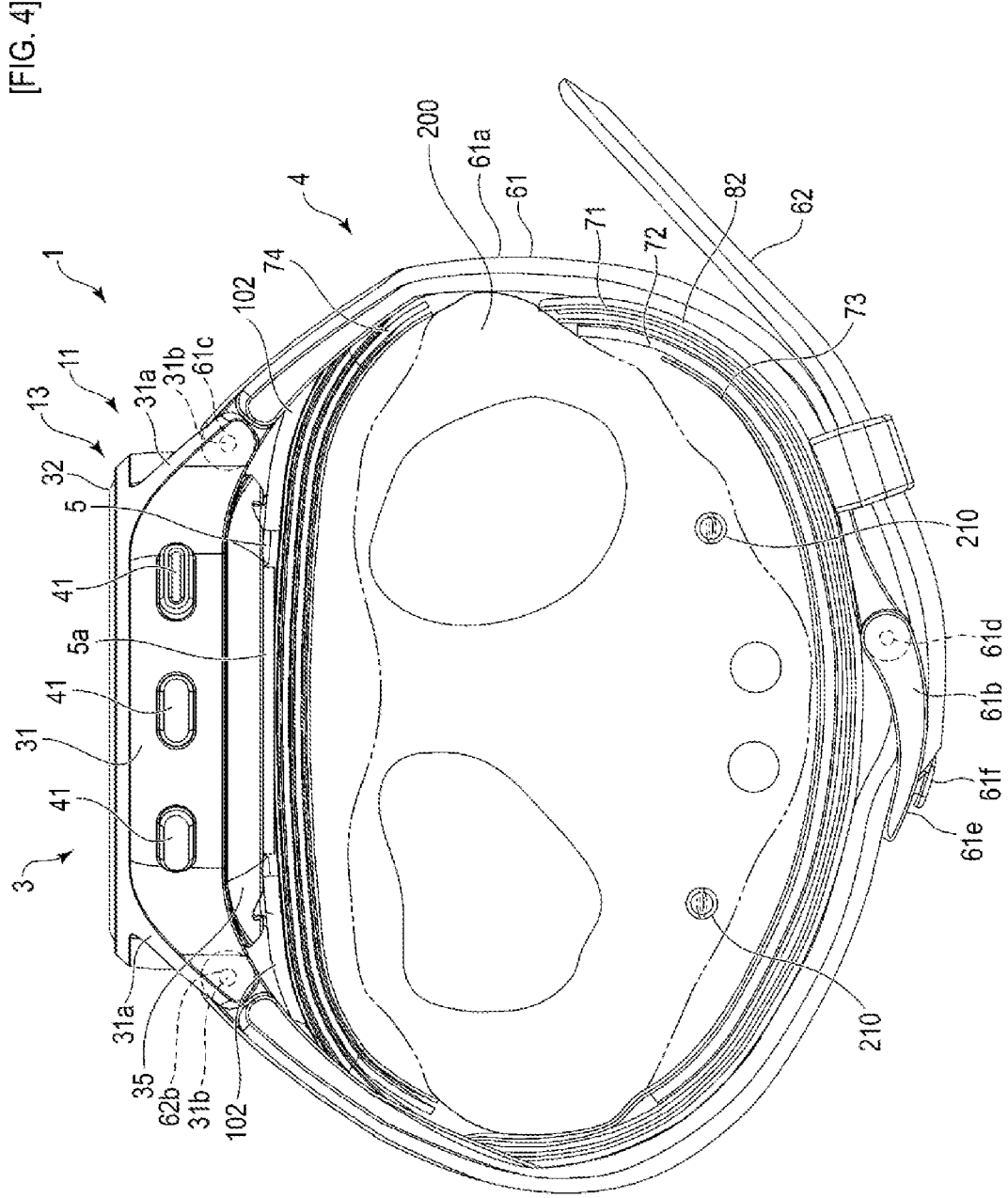
[FIG. 4]

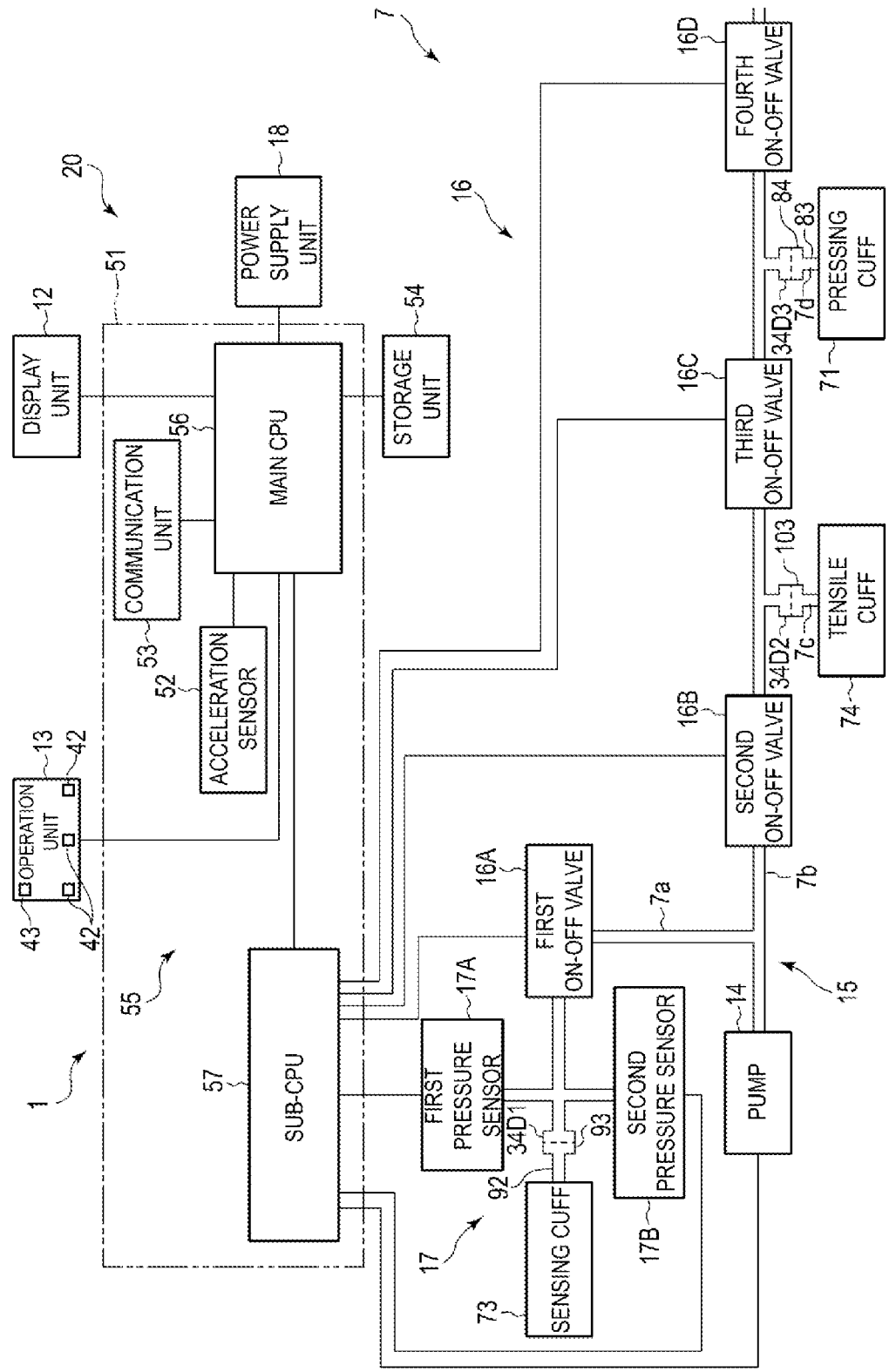

[FIG. 6]
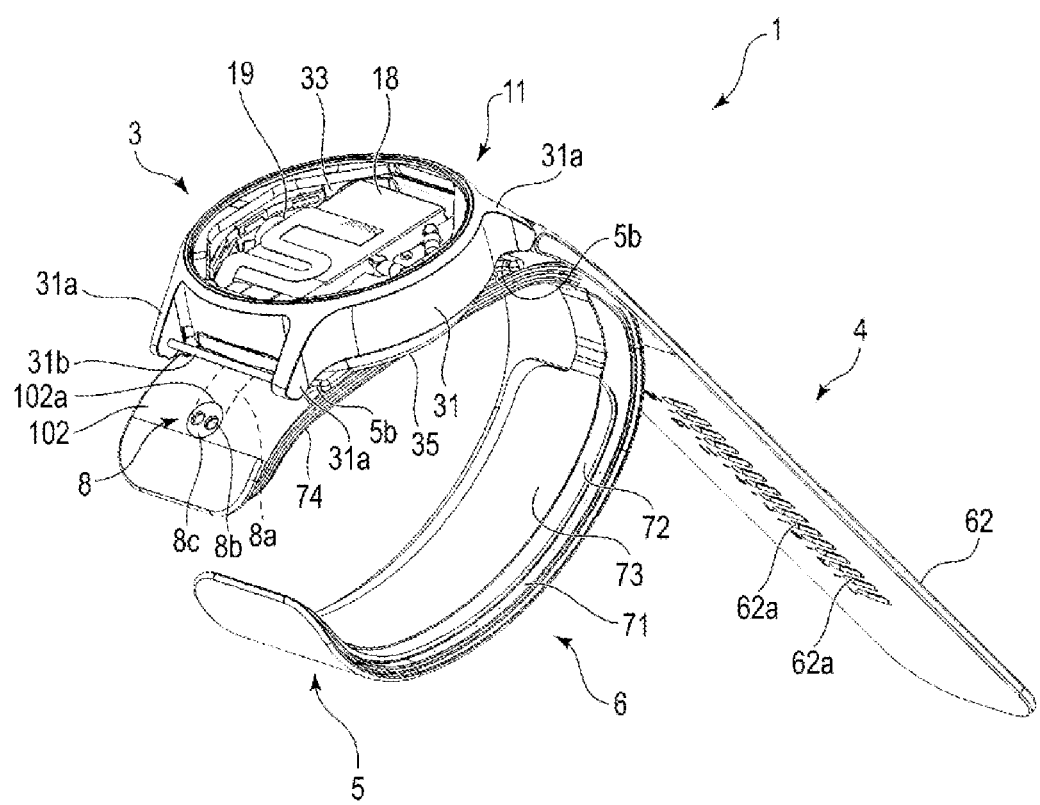

[FIG. 7]
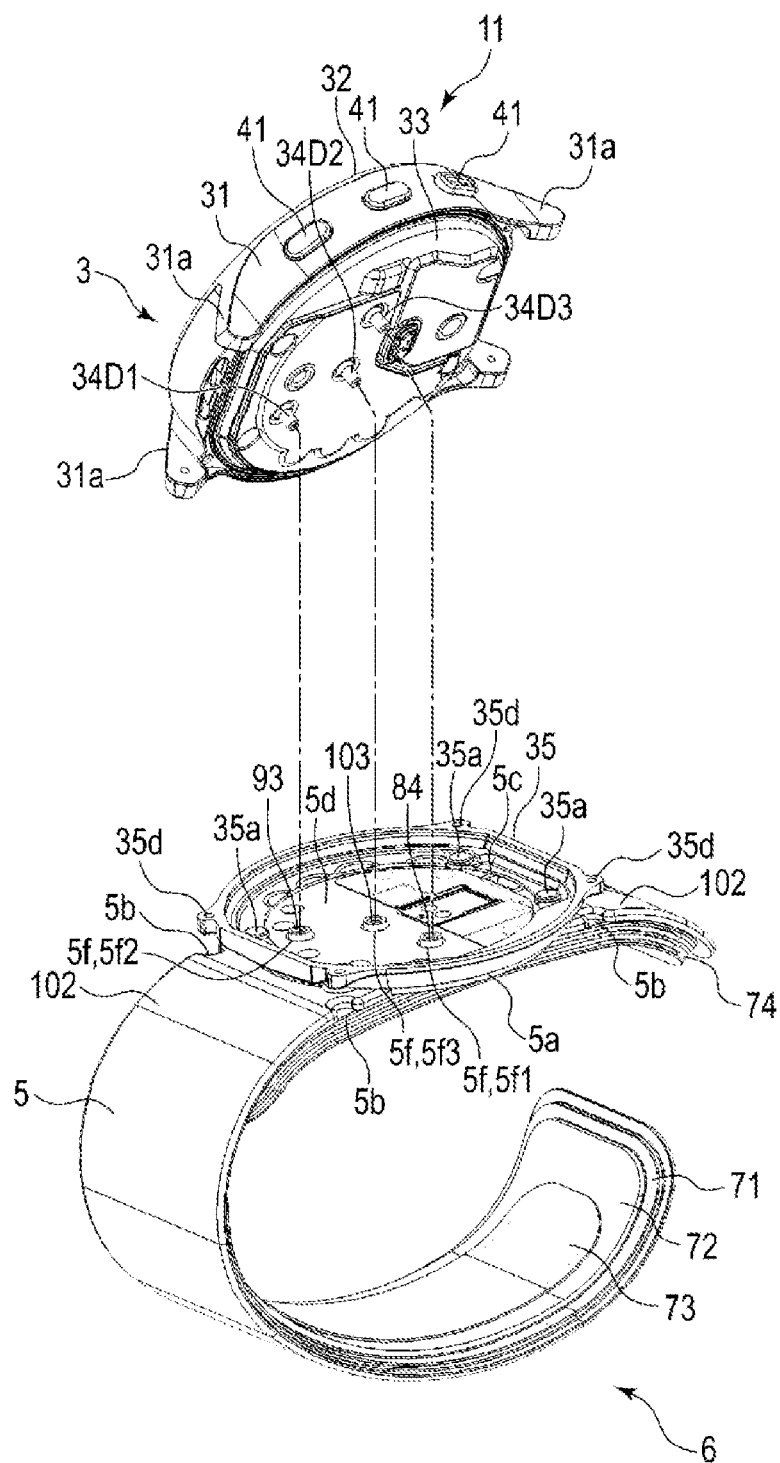

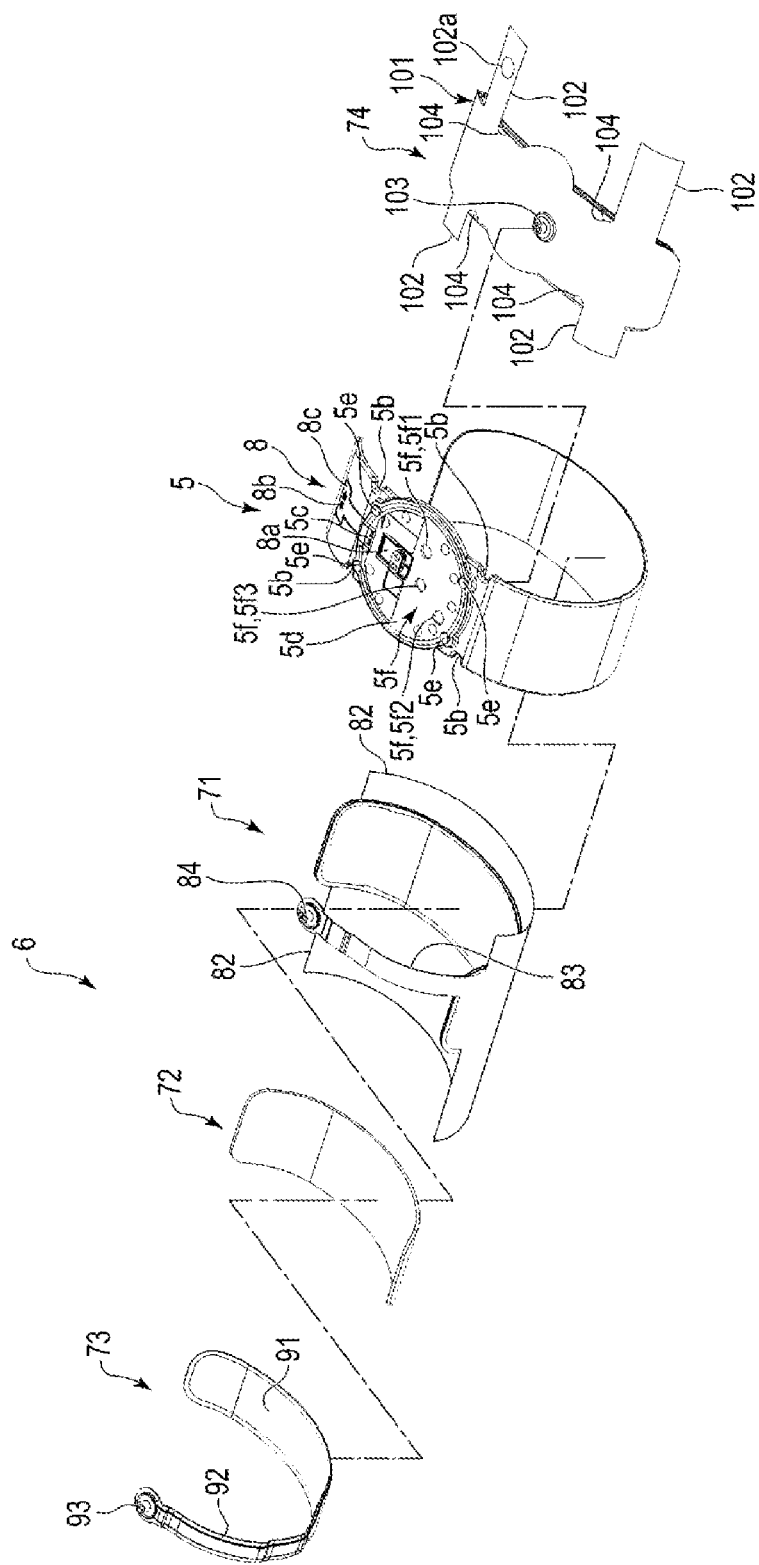

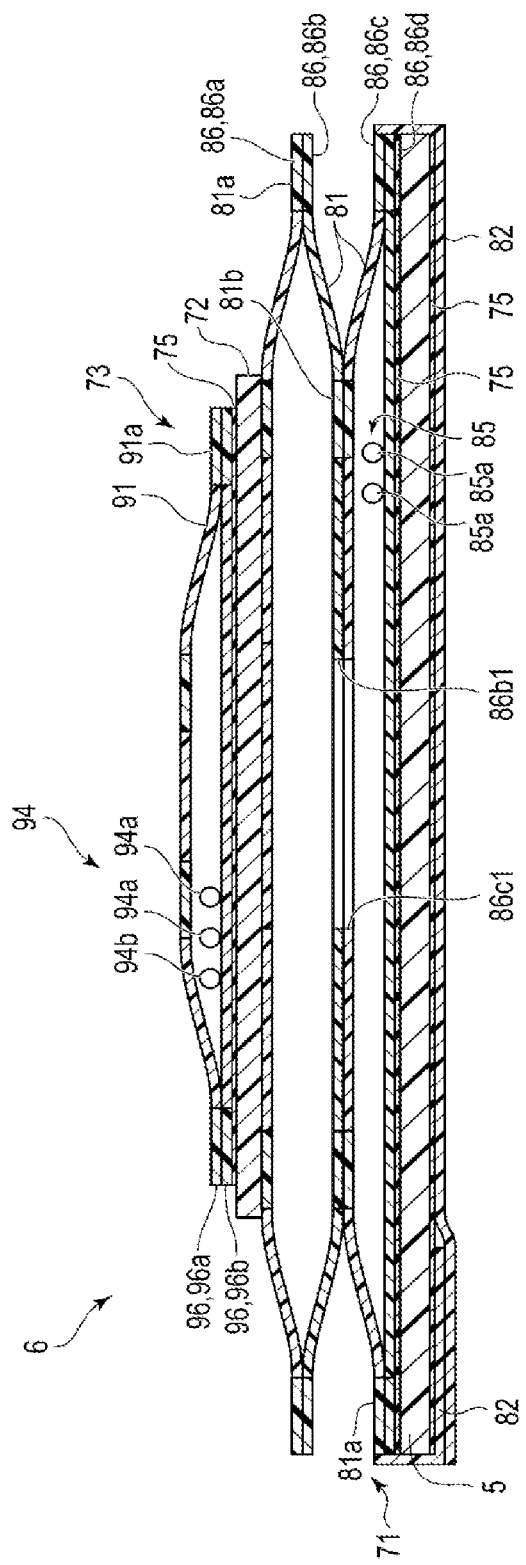

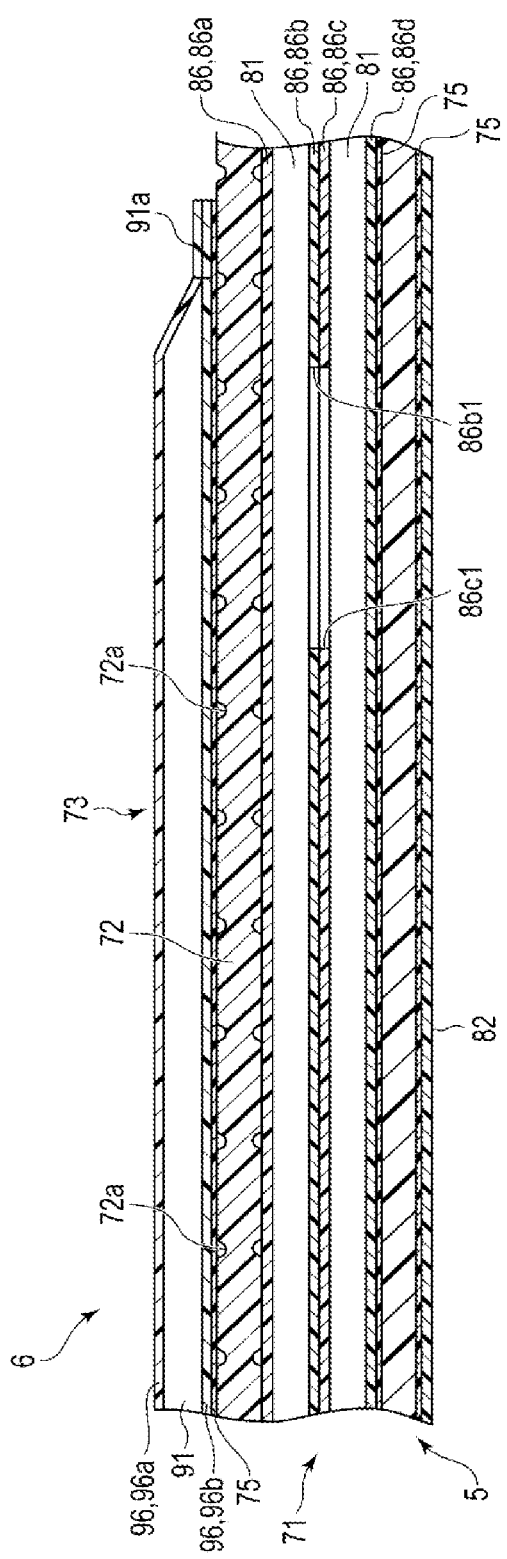

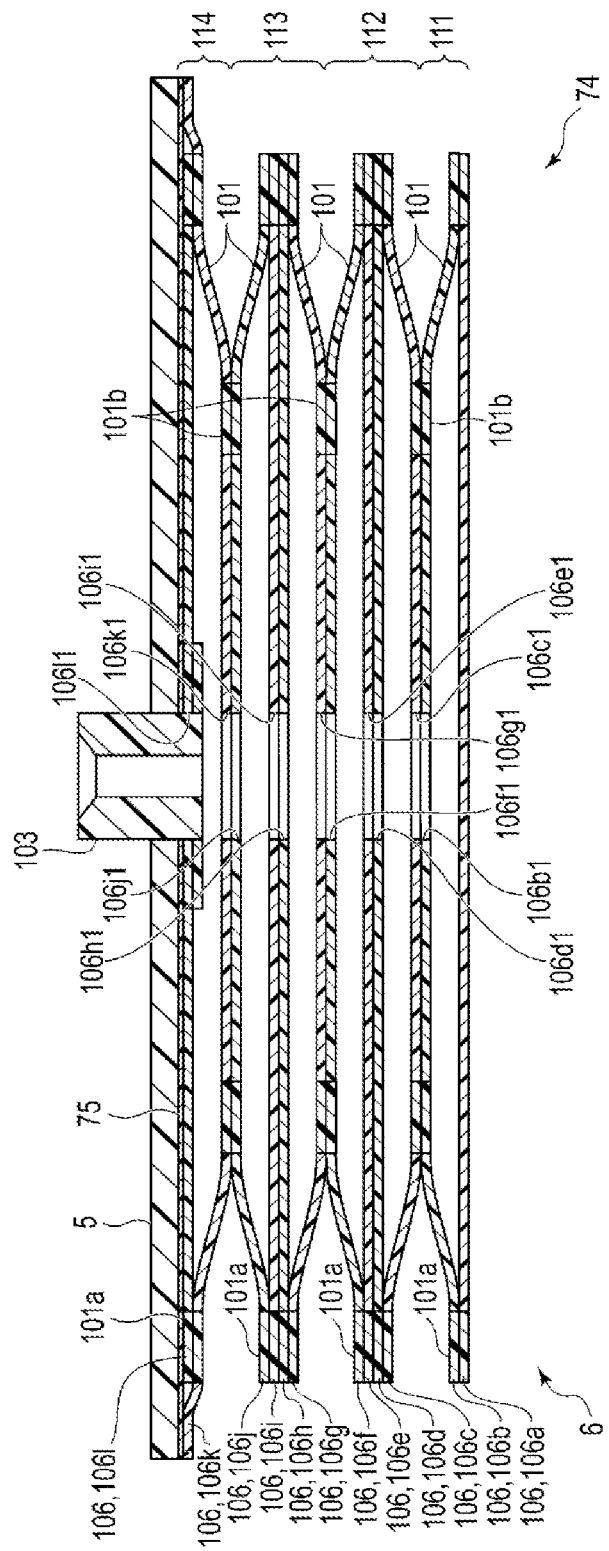
[FIG. 11]

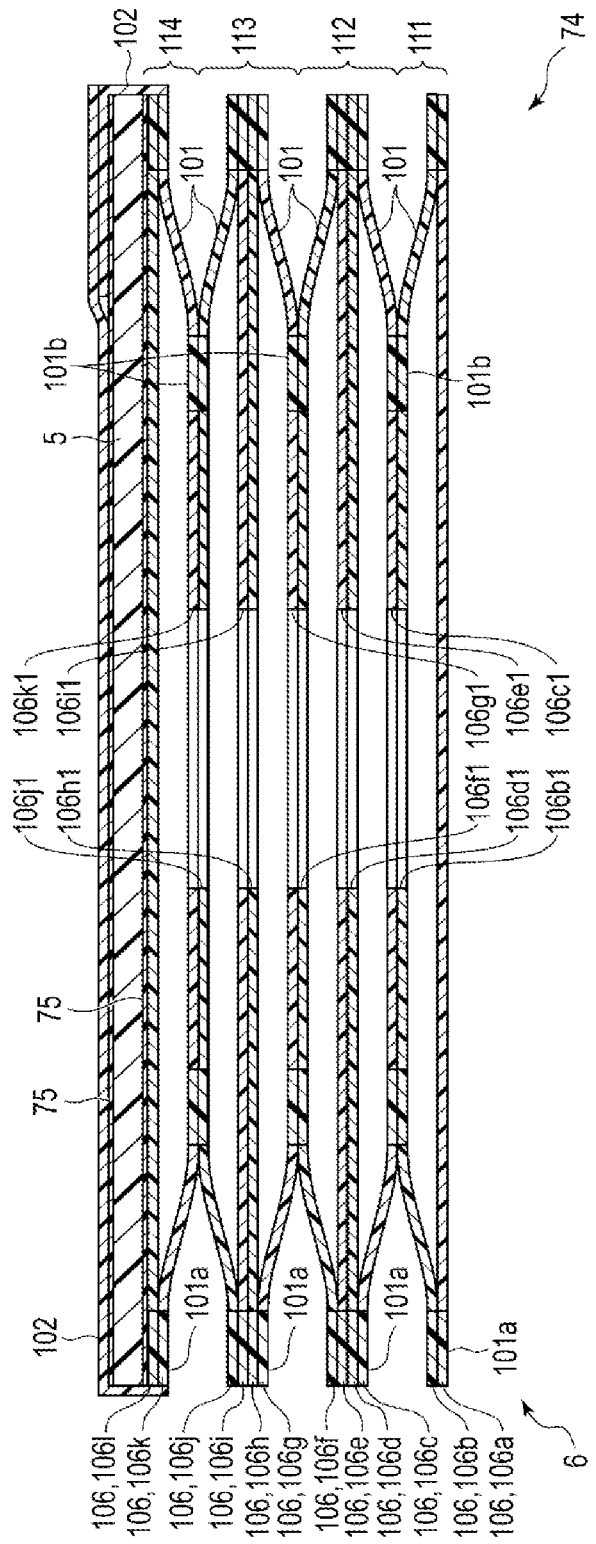

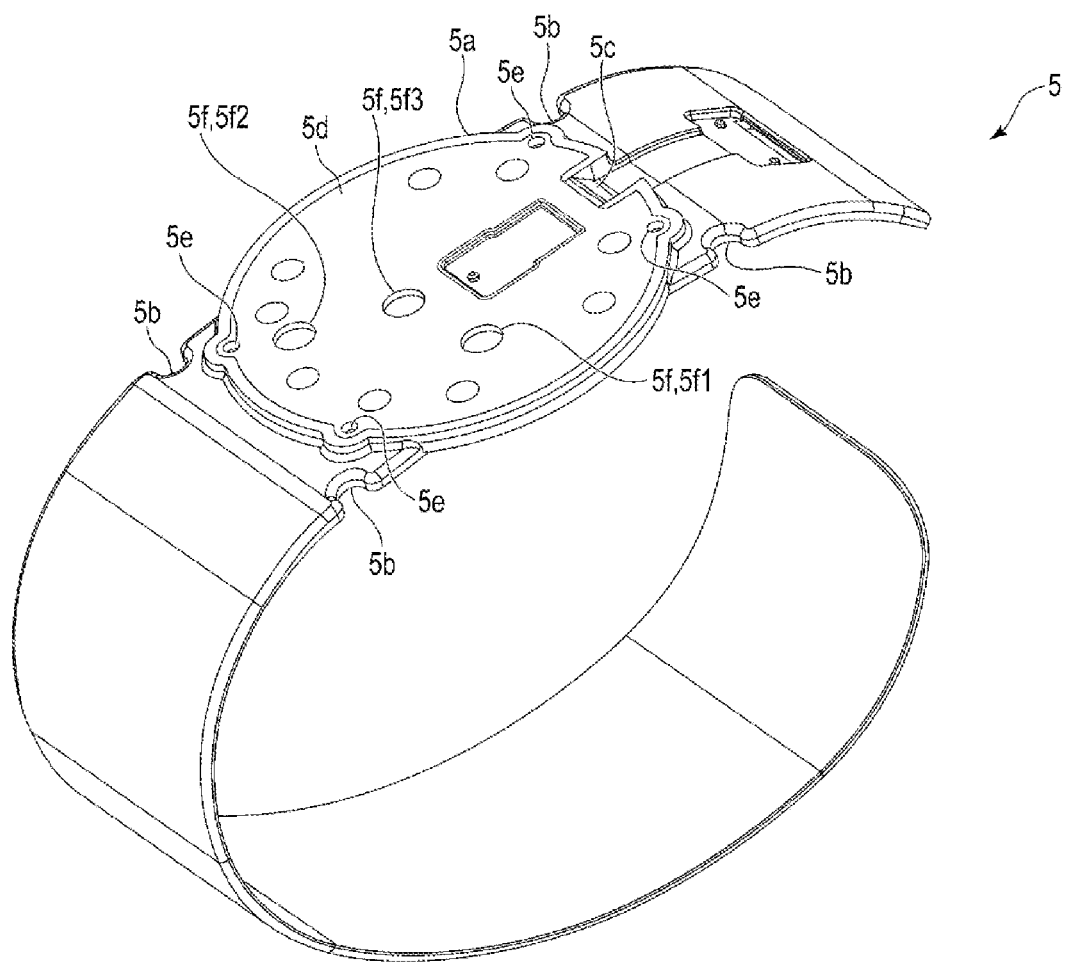
[FIG. 13]

[FIG. 14]
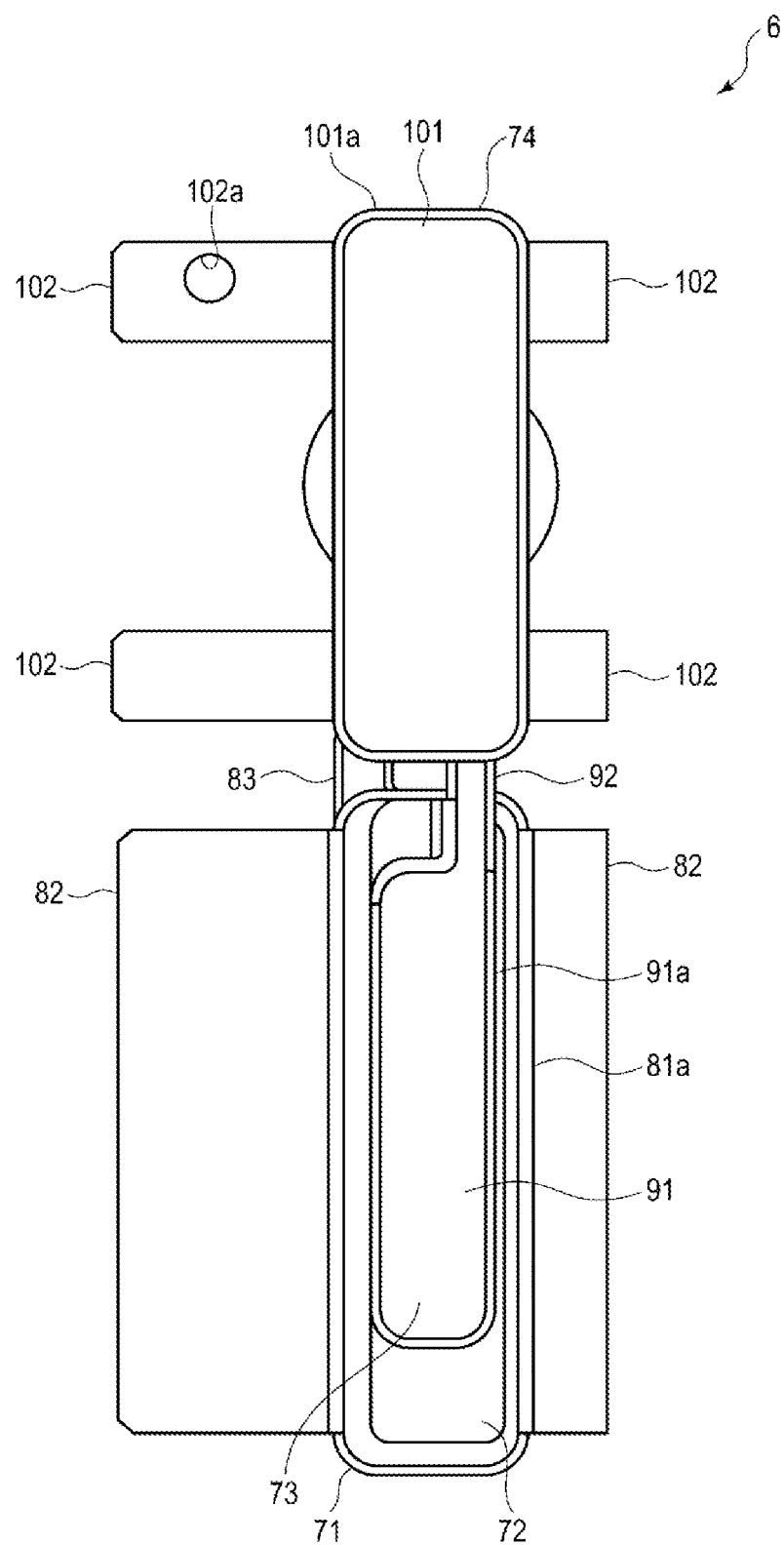

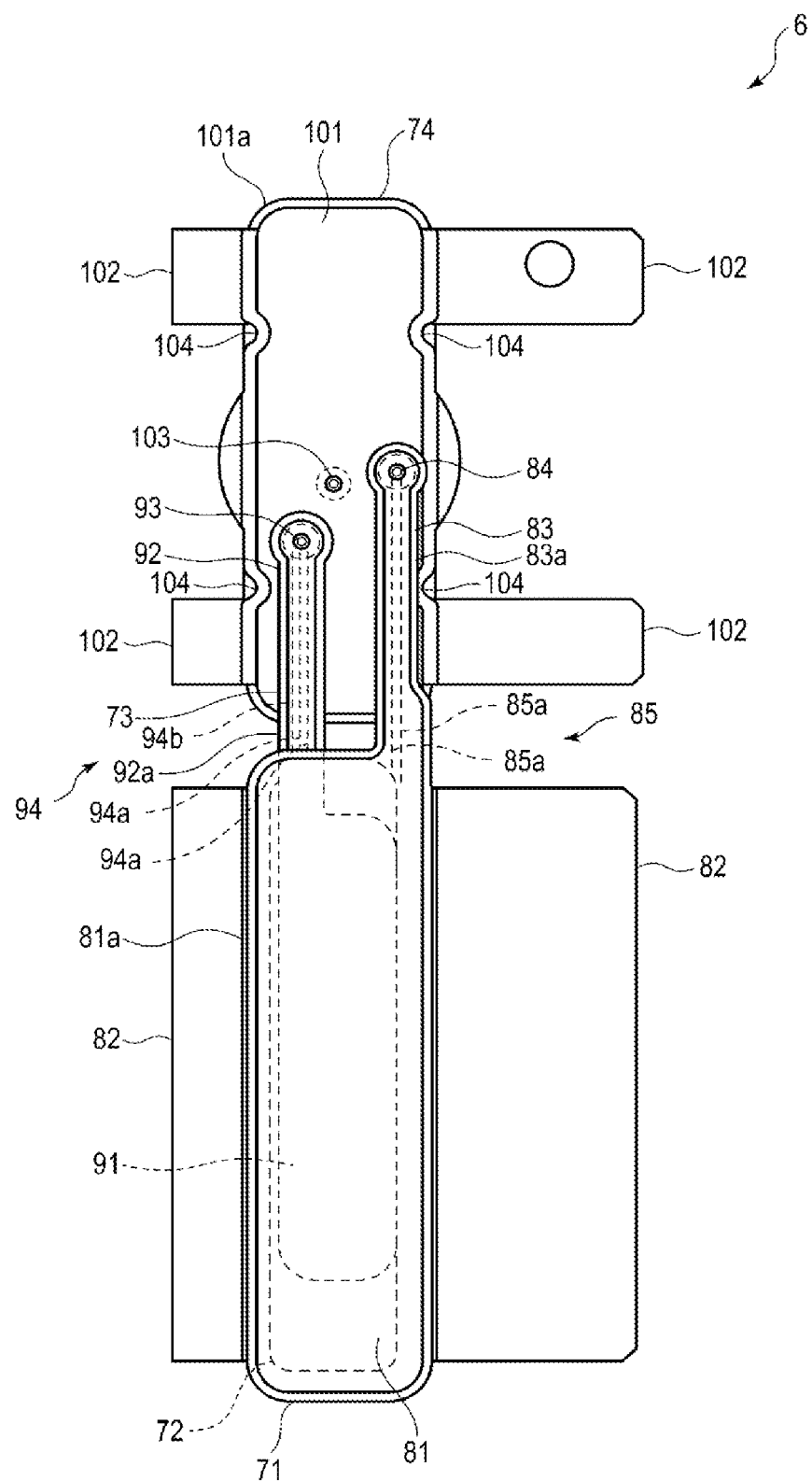
[FIG. 15]

[FIG. 16]
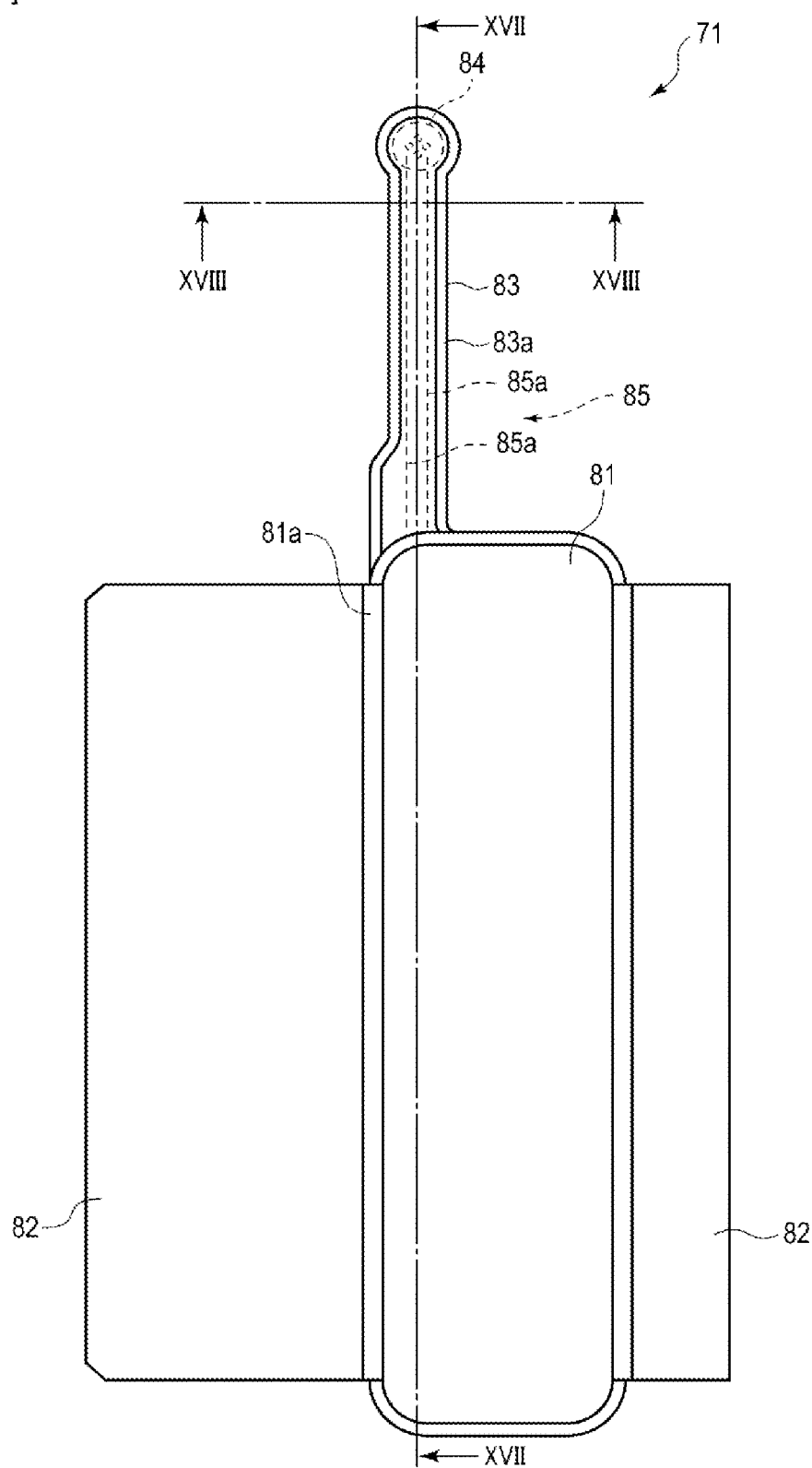

[FIG. 17]
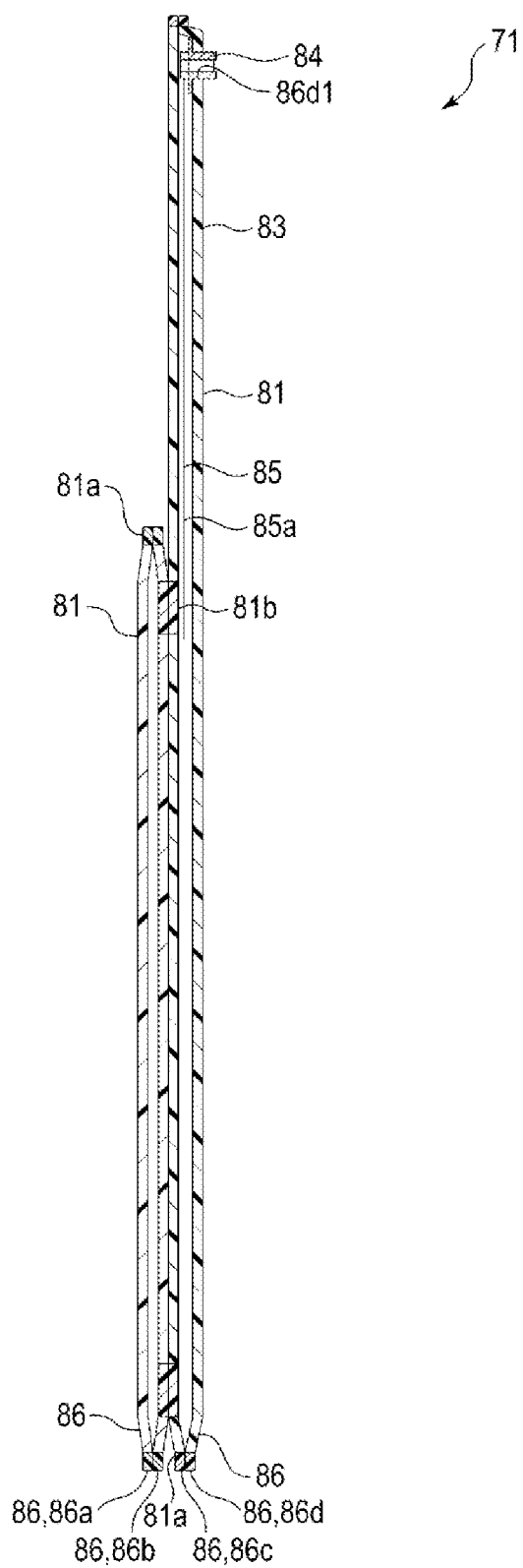

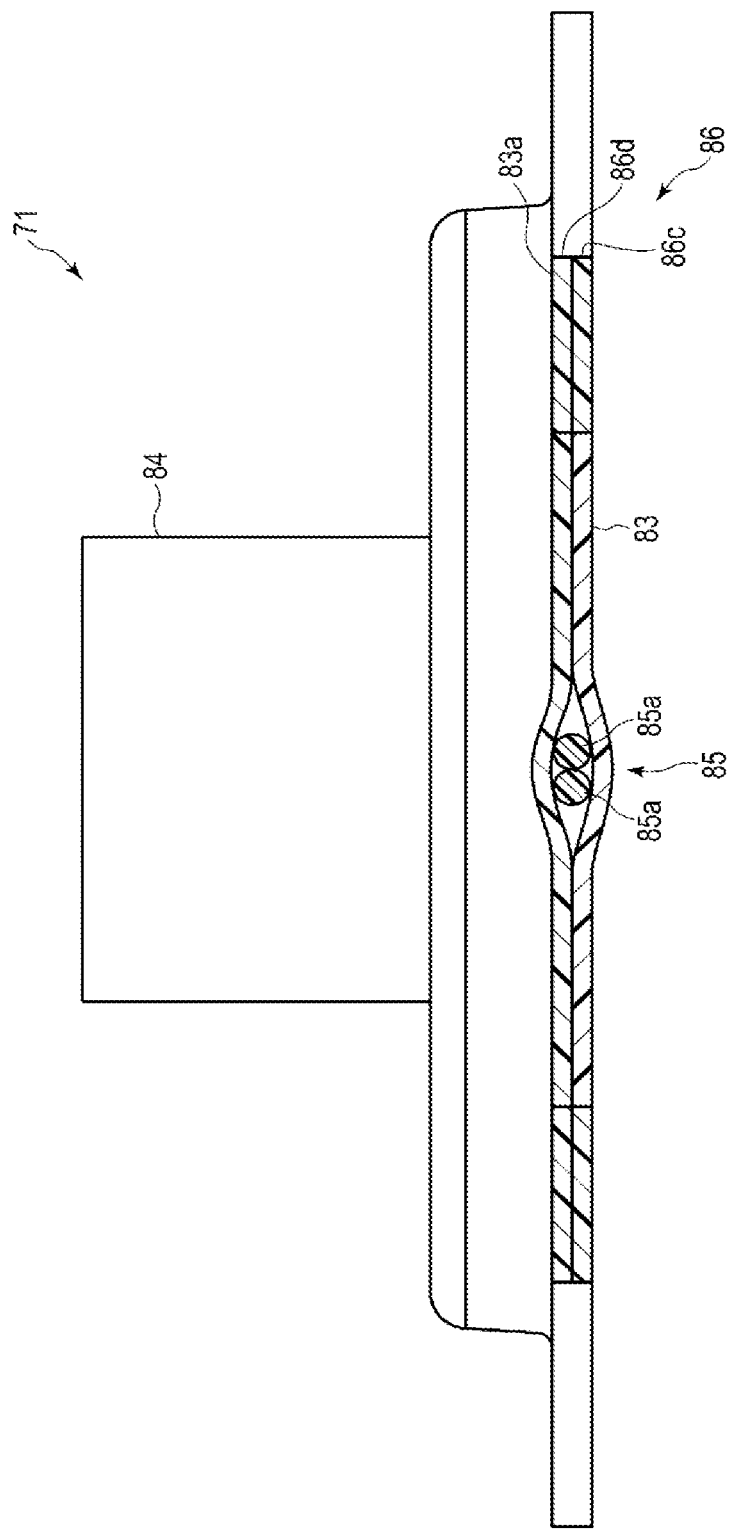

[FIG. 19]
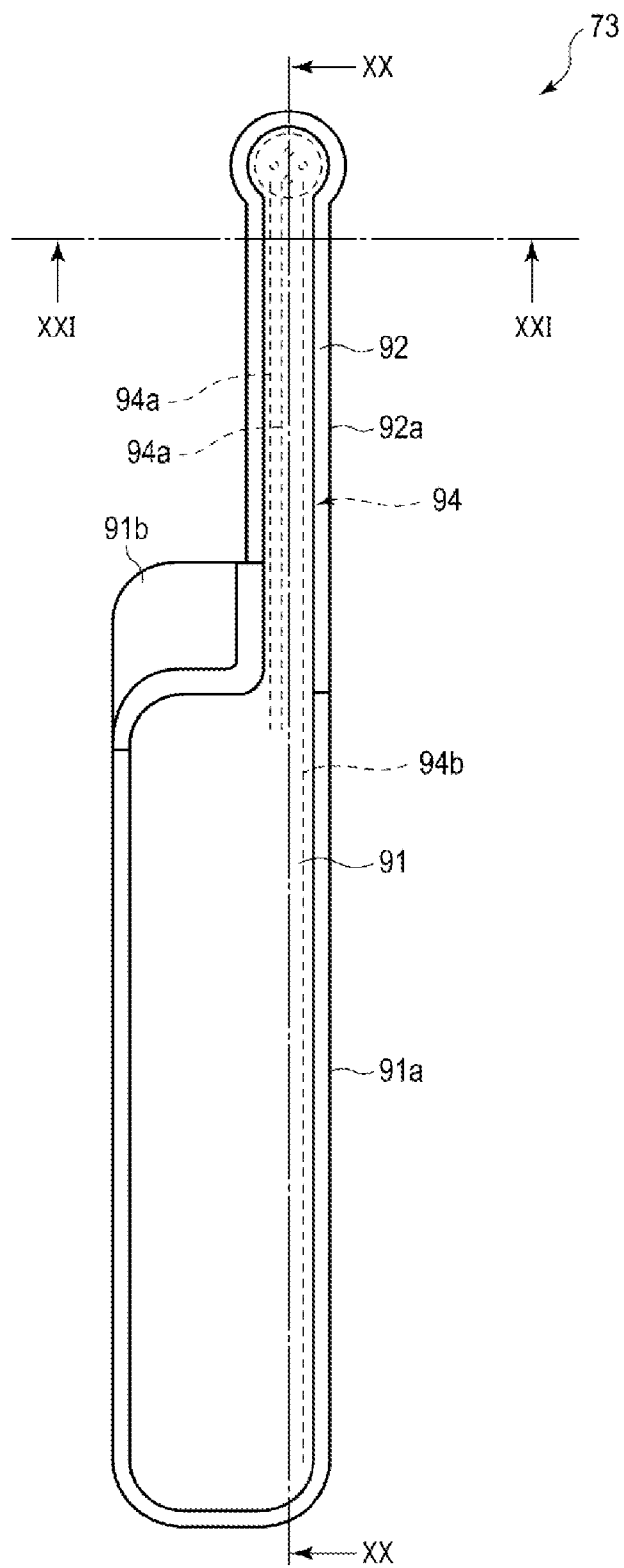

[FIG. 20]
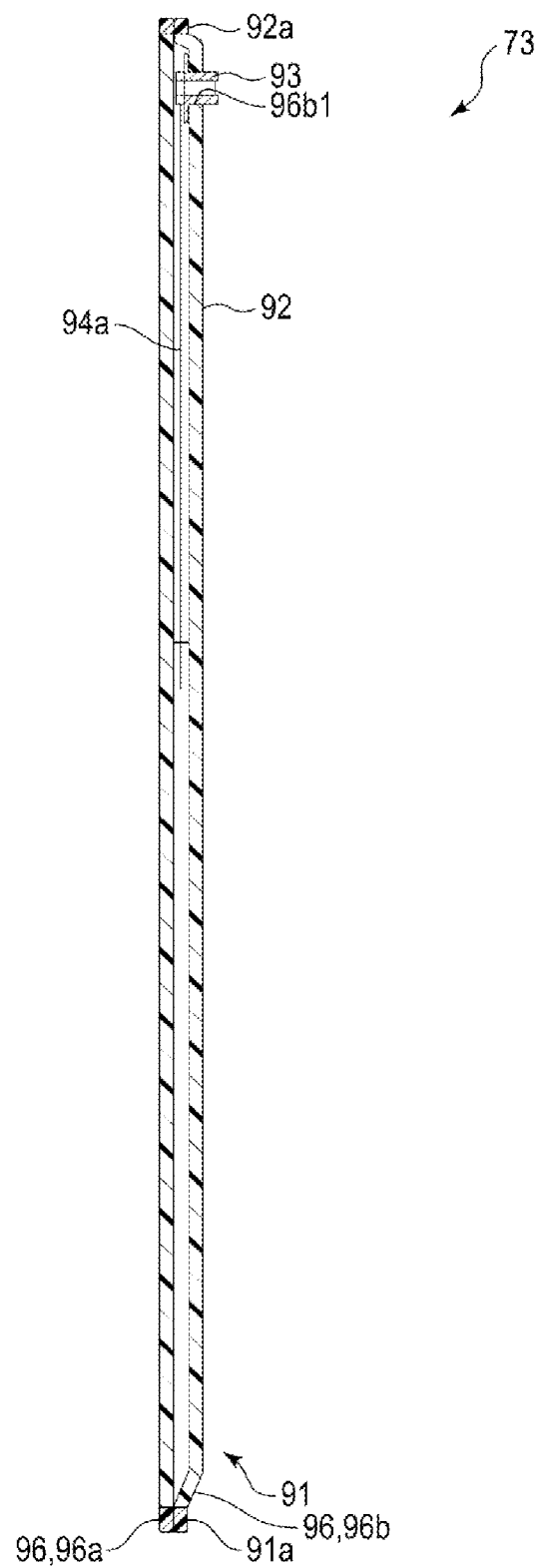

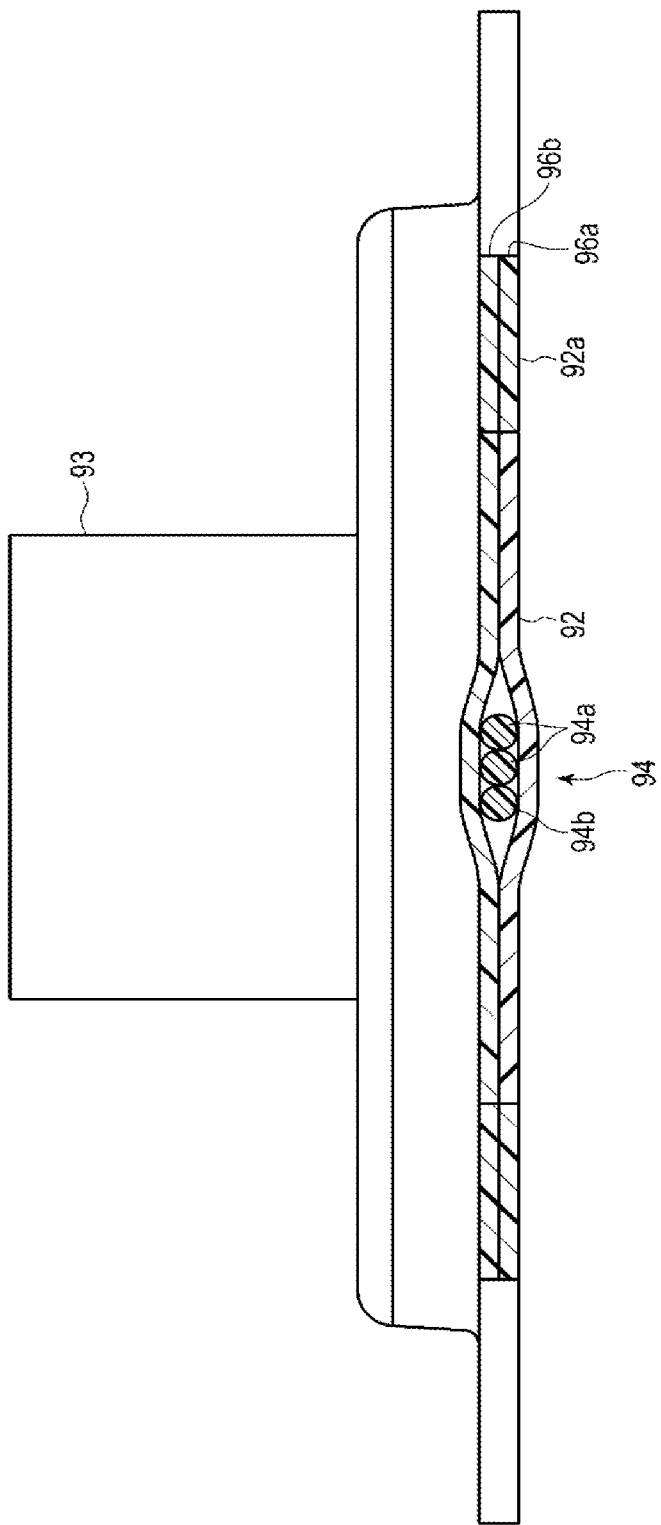
[FIG. 21]

[FIG. 22]
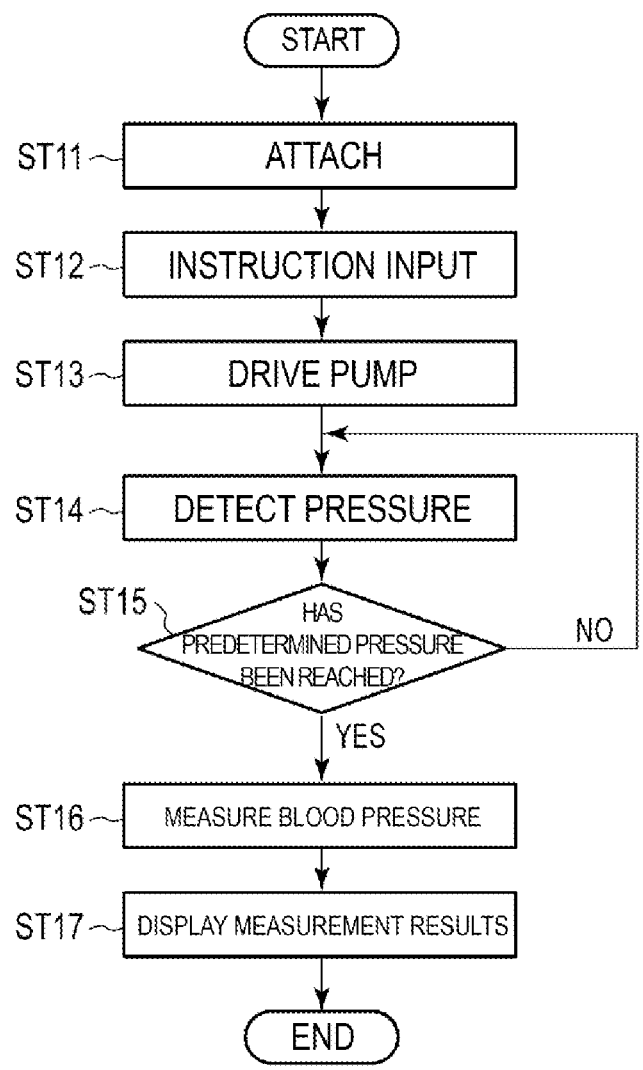

[FIG. 23]
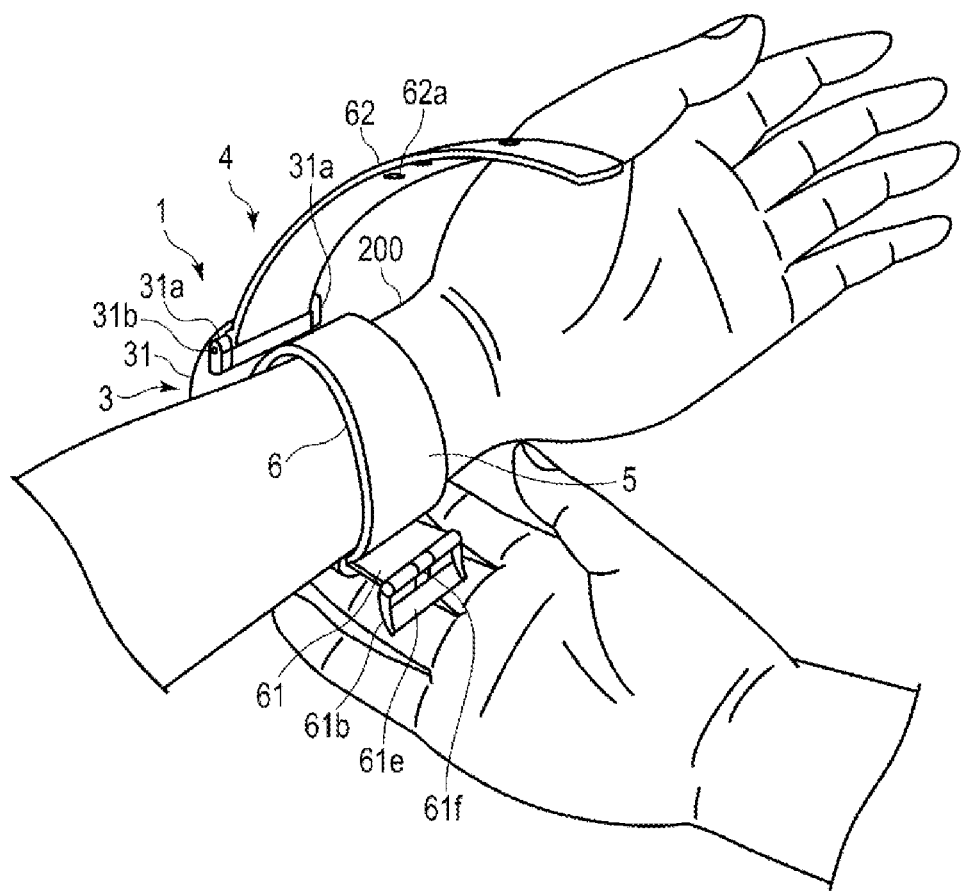

[FIG. 24]
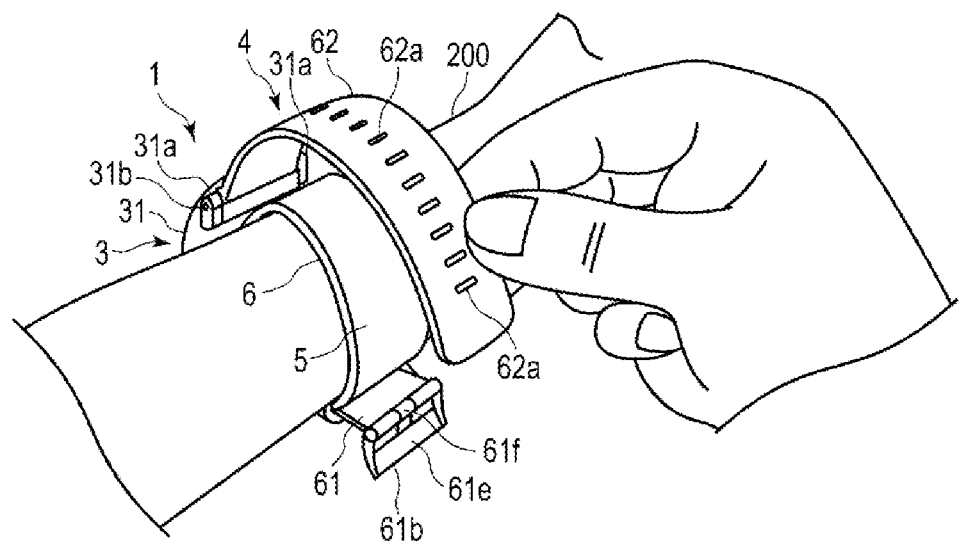
[FIG. 25]
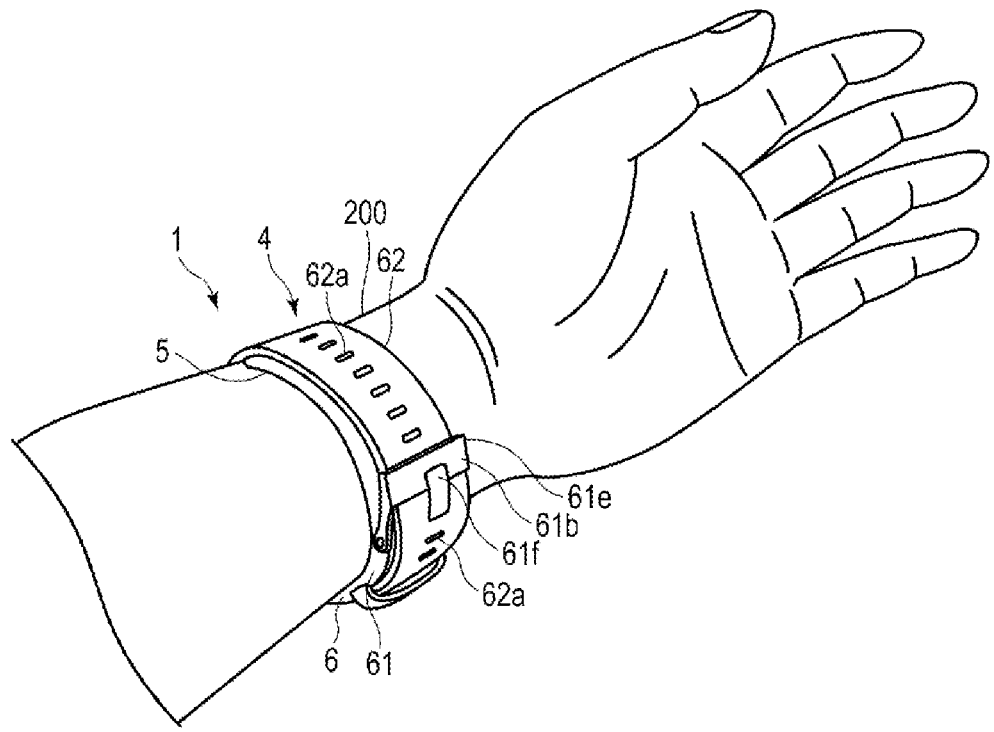

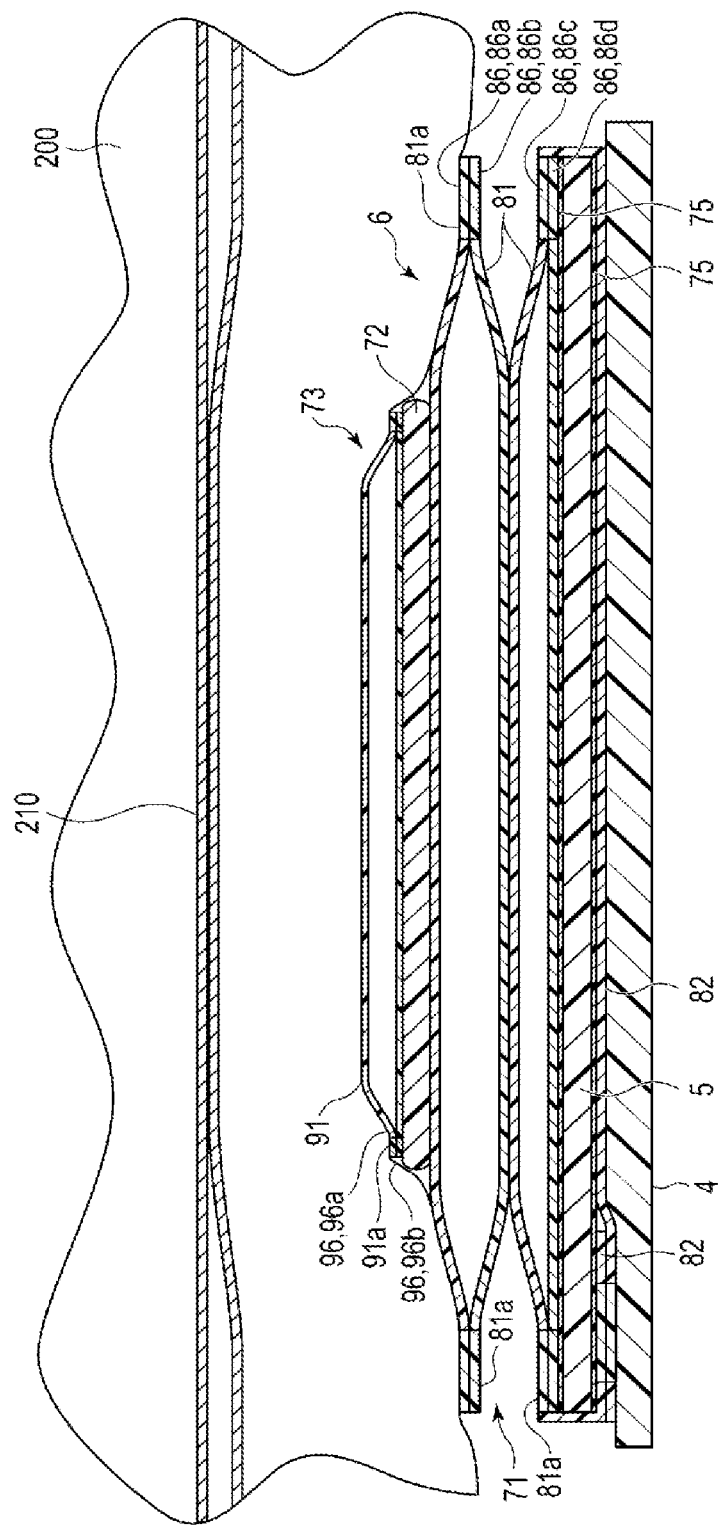
[FIG. 26]

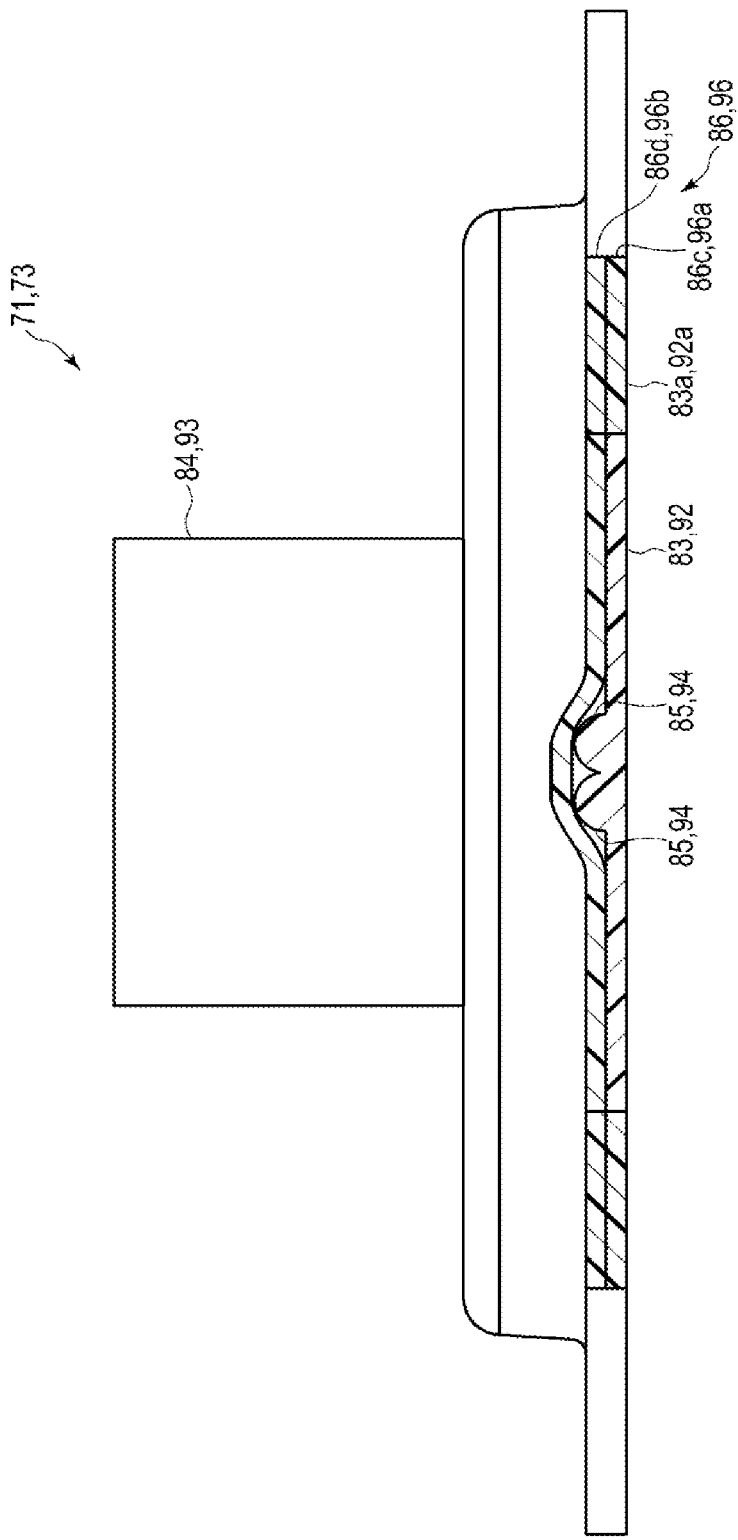

BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/048029, filed Dec. 9, 2019, which application claims priority to Japan Patent Application No. 2018-246102, filed Dec. 27, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor. As an example of a cuff used in such a blood pressure measurement device, the technology described in JP H11-309119 A is known in which a plurality of air bags are inflated to compress an artery.

As such a blood pressure measurement device, for example, a so-called integral type is known in which a cuff is integrated with a device body supplying a fluid to the cuff. Such blood pressure measurement devices have the problem that when wrinkles, folds, or the like are generated in the cuff, the accuracy of the measured blood pressure measurement result is reduced. There is also a demand for blood pressure measurement devices in which the cuff is inflated in the direction in which the blood vessels are occluded and the cuff comes into close contact with the wrist when the cuff is inflated.

Technology is known that uses a curler between a belt and a cuff, which brings the inflated cuff to close contact with the wrist. Such blood pressure measurement devices inflate the cuff after the cuff is brought into contact with the wrist by the belt and the curler to suitably occlude the blood vessels when the cuff is inflated.

CITATION LIST

Patent Literature

Patent Document 1: JP H11-309119 A

SUMMARY OF INVENTION

Technical Problem

A wearable device attached to the wrist has been proposed for the blood pressure measurement device described above, and there has been a demand for further miniaturization. However, providing a plurality of cuffs requires adequate space and thickness for placement of a tube or the like connecting the cuff and the pump. For example, the design is negatively affected when the tube connecting the cuff and the pump is disposed on the outer surface of a curler. Also, it is plausible to dispose the tube of another cuff between the curler and the cuff. However, by a tube being disposed between the curler and the cuff, the tube may inhibit cuff expansion, and the tube may be closed by being pressed on by another cuff.

Thus, an object of the present invention is to provide a blood pressure measurement device that can suitably inflate the cuff.

Solution to Problem

According to an aspect, a blood pressure measurement device is provided which includes, a device body internally including a pump and a flow path portion configured to supply a fluid from the pump to a secondary side, a curler including a cover portion that curves to follow a circumferential direction of the wrist from a hand back side of the wrist along one side of the wrist to a region on a hand palm-side of the wrist where at least an artery resides, and the cover portion is configured to fix the device body to the hand back side of the wrist, a belt provided on the device body, and configured to cover an outer circumferential surface of the curler, a pressing cuff including a first bag-like structure, a first flow path body, and a first connection portion, the first bag-like structure formed by joining two sheet members formed of a resin material, fixed to an inner circumferential surface of the hand palm-side of the wrist of the curler, and configured to be inflated by a fluid supplied from the pump, the first flow path body integrally formed with the first bag-like structure by joining the two sheet members forming the first bag-like structure facing the curler, configured to fluidly connect the pump and the first bag-like structure, and including a leading end disposed on the wrist side of the cover portion, the first connection portion provided on the leading end of the first flow path body, and configured to be inserted in the cover portion and connected to the flow path portion, a back plate fixed on the bag-like structure on the wrist side of the pressing cuff, and curving to follow along the circumferential direction of the wrist, a sensing cuff including a second bag-like structure, a second flow path body, and a second connection portion, the second bag-like structure formed by joining two sheet members, fixed to a main surface of the wrist side of the back plate, and configured to be inflated by fluid supplied from the pump, the second flow path body formed integrally with the second bag-like structure by joining the two sheet members forming the second bag-like structure, configured to fluidly connect the pump and the second bag-like structure, and including a leading end disposed on the wrist side of the cover portion, and the second connection portion provided on the leading end of the second flow path body, and configured to be inserted in the cover portion and connected to the flow path portion, and a tensile cuff including a third bag-like structure and a third connection portion, the third bag-like structure formed by joining two sheet members, fixed to an inner circumferential surface of the hand back side of the wrist of the curler, and configured to be inflated by fluid supplied from the pump, and the third connection portion provided on the third bag-like structure facing the curler, and configured to be inserted in the cover portion and connected to the flow path portion.

Here, the fluid includes a liquid and air. The bag-like structure is configured to be inflated by fluid, and is an air bag in a case where the fluid is air.

According to this aspect, the tensile cuff is disposed on the hand back side of the curler where the device body is provided, the pressing cuff and the sensing cuff are provided on the hand palm-side, and the flow path portion of the device body and the first bag-like structure and the second bag-like structure are connected through the first flow path body and the second flow path body. In addition, the first flow path body and the second flow path body are constituted by joining two sheet members.

Thus, the thickness of the first flow path body and the thickness of the second flow path body correspond to the thickness of the two sheet members. With such a configuration, the blood pressure measurement device can prevent the first flow path body and the second flow path body affecting the expansion of the tensile cuff even when the first flow path body and the second flow path body are disposed between the curler and the tensile cuff. In addition, because the first flow path body and the second flow path body are constituted by joining the two sheet members, deformation of the first flow path body and the second flow path body in the thickness direction thereof is suppressed. Thus, the first flow path body and the second flow path body are suppressed from being closed due to the expansion of the tensile cuff.

In addition, because the first flow path body and the second flow path body are disposed between the curler and the tensile cuff, the first flow path body and the second flow path body can be prevented as much as possible from being exposed to the outside. Thus, the blood pressure measurement device can be made smaller in size and design can be improved. Furthermore, because the first connection portion and the second connection portion are pressed to the device body side by the tensile cuff, the first connection portion and the second connection portion can be prevented from detaching from the flow path portion.

In the blood pressure measurement device according to the one aspect described above, the blood pressure measurement device is provided in which the pressing cuff includes a first thread member at least provided in the first flow path body, and the sensing cuff includes a second thread member at least disposed in the second flow path body.

According to this aspect, because the first thread member and the second thread member are disposed in the first flow path body and the second flow path body, respectively, a gap is formed between the two sheet members forming the first flow path body and the second flow path body. Thus, even in a case where the first flow path body and the second flow path body are pressed by the wrist when the tensile cuff is inflated or when the blood pressure measurement device is attached on the wrist, a gap is formed between the two sheet members by the first thread member and the second thread member. Thus the first flow path body and the second flow path body are prevented from being closed.

In the blood pressure measurement device according to the one aspect described above, the blood pressure measurement device is provided in which the second thread member includes a first thread disposed in the second flow path body and a second thread that is formed to be longer than the first thread and is disposed in the second flow path body and the second bag-like structure.

According to this aspect, a gap can be formed between the sheet members by the first thread and the second thread in both the second flow path body and the second bag-like structure. Thus, with the blood pressure measurement device, the sensing cuff can be reliably and suitably inflated, and more suitable blood pressure measurement can be performed.

In the blood pressure measurement device according to the one aspect described above, the blood pressure measurement device is provided in which the second thread member includes two of the first threads and one of the second thread.

According to this aspect, the two first threads and the one second thread are disposed in the second flow path body, and the one second thread is disposed in the second bag-like structure. Thus, a gap is formed between adjacent threads even when the sheet members are pressed by an external force in the direction pressing them tightly together. Thus, by the three threads, a gap can be formed between the sheet members of the second bag-like structure, with the volume of the second flow path body being reduced and the volume of the second bag-like structure being not reduced as much as possible. Thus, with the blood pressure measurement device, the second bag-like structure can be suitably inflated required for blood pressure measurement with the sensing cuff.

In the blood pressure measurement device according to the one aspect described above, the blood pressure measurement device is provided in which the first thread member includes at least two threads disposed in the first flow path body.

According to this aspect, the two threads are provided on the first flow path body. Thus, a gap is formed between adjacent threads even when the sheet members are pressed by an external force in the direction pressing them tightly together. Thus, with the blood pressure measurement device, the pressing cuff can be suitably inflated.

In the blood pressure measurement device according to the one aspect described above, the blood pressure measurement device is provided in which the first bag-like structure is joined in a rectangular frame shape at inside from an outer peripheral edge of the first bag-like structure and is fluidly continuous inside a joined join portion, and the first thread member is disposed from the first flow path body to the join portion.

According to this aspect, because the first thread member is disposed from the first flow path body to the join portion where the first bag-like structure is joined, air can be supplied to the portion where the first bag-like structures are fluidly continuous, and the first bag-like structure can be suitably inflated.

In the blood pressure measurement device according to the one aspect described above, the blood pressure measurement device is provided in which the first thread member and the second thread member are set with a thread diameter of equal to or less than a sum of a thickness of the two sheet members.

According to this aspect, the thread diameter of the first thread member and the second thread member are the sum of the thickness of the two sheet members or less. Thus, the surface of the pressing cuff and the sensing cuff can be prevented from bulging due to the first thread member and the second thread member. Also, in a case where the sensing cuff with which blood pressure measurement is performed has a configuration in which it comes into close contact with the wrist, a reduction in the tactile sensation of the sensing cuff can be prevented and the wrist being compressed by the second thread member disposed in the bag-like structure of the sensing cuff can be prevented.

In the blood pressure measurement device according to the one aspect described above, the blood pressure measurement device is provided in which the first connection portion and the second connection portion are nipples with an inner diameter that allows the first thread member and the second thread member to be inserted, and the first thread member and the second thread member are formed separate from the sheet member.

According to this aspect, the first thread member and the second thread member can be inserted from the nipples, making manufacturing easier. In addition, because the pressing cuff and the sensing cuff are disposed curving to the inner circumferential surface of the curler, a difference is formed between the inner and outer circumference of the two sheet members, and the first thread member and the second thread member are sandwiched and held by the two sheet members. Thus, movement of the first thread member and the second thread member can be suppressed.

Advantageous Effects of Invention

The present invention can provide a blood pressure measurement device that can suitably inflate a cuff.

BRIEF DESCRIPTION OF DRAWINGS

FIG. 1 is a perspective view illustrating a configuration of a blood pressure measurement device according to a first embodiment of the present invention.

FIG. 2 is an exploded perspective view illustrating the configuration of the blood pressure measurement device.

FIG. 3 is a side view illustrating the configuration of the blood pressure measurement device.

FIG. 4 is an explanatory diagram illustrating a state in which the blood pressure measurement device is attached to the wrist.

FIG. 5 is a block diagram illustrating the configuration of the blood pressure measurement device.

FIG. 6 is a perspective view illustrating the configuration of the blood pressure measurement device.

FIG. 7 is an exploded perspective view illustrating the configuration of the blood pressure measurement device.

FIG. 8 is an exploded perspective view illustrating the configuration of a curler and a cuff structure of the blood pressure measurement device.

FIG. 9 is a cross-sectional view illustrating the configuration of the curler and the cuff structure of the blood pressure measurement device.

FIG. 10 is a cross-sectional view illustrating the configuration of the curler and the cuff structure of the blood pressure measurement device.

FIG. 11 is a cross-sectional view illustrating the configuration of a tensile cuff of the blood pressure measurement device.

FIG. 12 is a cross-sectional view illustrating the configuration of a tensile cuff of the blood pressure measurement device.

FIG. 13 is a perspective view illustrating the configuration of the curler of the blood pressure measurement device.

FIG. 14 is a plan view illustrating the configuration of the cuff structure of the blood pressure measurement device.

FIG. 15 is a plan view illustrating the configuration of the cuff structure.

FIG. 16 is a plan view illustrating the configuration of a pressing cuff of the blood pressure measurement device.

FIG. 17 is a cross-sectional view illustrating the configuration of the pressing cuff.

FIG. 18 is a cross-sectional view illustrating the configuration of the pressing cuff.

FIG. 19 is a plan view illustrating the configuration of a sensing cuff of the blood pressure measurement device.

FIG. 20 is a cross-sectional view illustrating the configuration of the sensing cuff.

FIG. 21 is a cross-sectional view illustrating the configuration of the sensing cuff.

FIG. 22 is a flowchart illustrating an example of usage of the blood pressure measurement device.

FIG. 23 is a perspective view illustrating an example in which the blood pressure measurement device is attached to the wrist.

FIG. 24 is a perspective view illustrating an example in which the blood pressure measurement device is attached to the wrist.

FIG. 25 is a perspective view illustrating an example in which the blood pressure measurement device is attached to the wrist.

FIG. 26 is a cross-sectional view schematically illustrating a state in which the blood pressure measurement device is attached to the wrist.

FIG. 27 is a cross-sectional view illustrating the configuration of a pressing cuff and a sensing cuff according to a modified example of the present invention.

DESCRIPTION OF EMBODIMENTS

First Embodiment

An example of a blood pressure measurement device 1 according to a first embodiment of the present invention will be described below with reference to FIGS. 1 to 21.

FIG. 1 is a perspective view illustrating a configuration of the blood pressure measurement device 1 according to a first embodiment of the present invention. FIG. 2 is an exploded perspective view illustrating the configuration of the blood pressure measurement device 1. FIG. 3 is a side view illustrating the configuration of the blood pressure measurement device 1. FIG. 4 is an explanatory diagram illustrating a state in which the blood pressure measurement device 1 is attached to the wrist 200. FIG. 5 is a block diagram illustrating the configuration of the blood pressure measurement device 1. FIG. 6 is a perspective view illustrating the configuration of the blood pressure measurement device 1 with some configurations removed. FIG. 7 is an exploded perspective view illustrating the configuration of the blood pressure measurement device 1 with some configurations removed. FIG. 8 is an exploded perspective view illustrating the configuration of a curler 5 and a cuff structure 6 of the blood pressure measurement device 1. FIG. 9 is a cross-sectional view illustrating the configuration of the curler 5 and the cuff structure 6 of the blood pressure measurement device 1. FIG. 10 is a cross-sectional view illustrating the configuration of the curler 5 and the cuff structure 6 of the blood pressure measurement device 1. FIG. 11 is a cross-sectional view illustrating the configuration of a tensile cuff 74 of the blood pressure measurement device 1. FIG. 12 is a cross-sectional view illustrating the configuration of the tensile cuff 74 of the blood pressure measurement device 1. FIG. 13 is a perspective view illustrating the configuration of the curler 5 of the blood pressure measurement device 1. FIG. 14 is a plan view illustrating the configuration of the cuff structure 6 of the blood pressure measurement device 1 from the wrist 200 side. FIG. 15 is a plan view illustrating the configuration of the curler 5 of the cuff structure 6 on the inner circumferential surface side.

FIG. 16 is a plan view illustrating the configuration of a pressing cuff 71 of the blood pressure measurement device 1. FIG. 17 is a cross-sectional view illustrating the configuration of the pressing cuff 71, which is a line cross-section along XVII-XVII illustrated in FIG. 16. FIG. 18 is a cross-sectional view illustrating the configuration of the pressing cuff 71, which is a line cross-section along XVIII-XVIII illustrated in FIG. 16. FIG. 19 is a plan view illustrating the configuration of a sensing cuff 73 of the blood pressure measurement device 1. FIG. 20 is a cross-sectional view illustrating the configuration of the sensing cuff 73 of the blood pressure measurement device 1, which is a line cross-section along XX-XX illustrated in FIG. 19. FIG. 21 is a cross-sectional view illustrating the configuration of the sensing cuff 73, which is a line cross-section along XXI-XXI illustrated in FIG. 19.

The blood pressure measurement device 1 is an electronic blood pressure measurement device attached to a living body. The present embodiment will be described using an electronic blood pressure measurement device having an aspect of a wearable device attached to the wrist 200 of the living body.

As illustrated in FIGS. 1 to 6, the blood pressure measurement device 1 includes the device body 3, a belt 4 that fixes the device body 3 at the wrist, the curler 5 disposed between the belt 4 and the wrist, the cuff structure 6 including the pressing cuff 71, the sensing cuff 73, and the tensile cuff 74, a fluid circuit 7 fluidly connecting the device body 3 and the cuff structure 6, and a power feeding unit 8 provided on the curler 5.

As illustrated in FIGS. 1 to 6, the device body 3 includes, for example, a case 11, a display unit 12, an operation unit 13, a pump 14, the flow path portion 15, the on-off valve 16, the pressure sensor 17, a power supply unit 18, a vibration motor 19, and a control substrate 20. The device body 3 supplies a fluid to the cuff structure 6 using the pump 14, the on-off valve 16, the pressure sensor 17, the control substrate 20, and the like.

As illustrated in FIGS. 1 to 3, the case 11 includes an outer case 31, a windshield 32 covering an opening of the outer case 31 on the opposite side (outer side) to the wrist 200 side, a base portion 33 provided inside the outer case 31 on the wrist 200 side, a rear cover 35 covering the wrist 200 side of the outer case 31, and a sealing member 36 provided on the lower surface of the rear cover 35.

The outer case 31 is formed in a cylindrical shape. The outer case 31 includes pairs of lugs 31a provided at respective symmetrical positions in the circumferential direction of an outer circumferential surface, and spring rods 31b each provided between each of the two pairs of lugs 31a. The windshield 32 is, for example, a circular glass plate.

The base portion 33 holds the display unit 12, the operation unit 13, the pump 14, the on-off valve 16, the pressure sensor 17, the power supply unit 18, the vibration motor 19, and the control substrate 20. Additionally, the base portion 33 constitutes a portion of the flow path portion 15 that makes the pump 14 and the cuff structure 6 fluidly continuous.

The rear cover 35 is configured as an annular shape with an open center. The rear cover 35 covers the end portion on the outer peripheral edge side of the outer case 31 on the wrist 200 side. With the rear cover 35 configured as such being integrally assembled with the curler 5, the central opening is covered by the curler 5, and the rear cover 35 together with the curler 5 forms a rear lid covering the end portion of the outer case 31 on the wrist 200 side. Specifically, the rear cover 35 is fixed to the curler 5 with four first joining members 35a and fixed to the end portion of the outer case 31 on the wrist 200 side with four second joining members 35b. The rear cover 35 includes four hole portions 35c into which the first joining members 35a that are provided at the bottom portion and fixed to the curler 5 are inserted, and four hole portions 35d provided at four portions of the outer circumferential portion that radially project out, into which the second joining members 35b that are fixed to the outer case 31 are inserted.

The first joining members 35a and the second joining members 35b are members, such as a screw, a bolt, a machine screw, a rive, for mechanically joining two components. In the present embodiment, the first joining members 35a and the second joining members 35b are screws.

The sealing member 36 is a double-sided tape, for example, formed in the shape of the region of the rear cover 35 that comes into contact with the curler 5. The sealing member 36 seals between the curler 5 and the rear cover 35 by being provided between the curler 5 and the rear cover 35.

The display unit 12 is disposed on the base portion 33 of the outer case 31 and directly below the windshield 32. As illustrated in FIG. 5, the display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIGS. 1 and 5. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base portion 33 and protrude from the outer circumferential surface of the outer case 31. The plurality of buttons 41 and a plurality of the sensors 42 are supported by the base portion 33. The touch panel 43 is integrally provided on the windshield 32, for example.

The pump 14 is, for example, a piezoelectric pump. The pump 14 compresses air and supplies compressed air to the cuff structure 6 through the flow path portion 15. The pump 14 is electrically connected to the control substrate 20.

The flow path portion 15 constitutes the flow path connecting from the pump 14 to the pressing cuff 71 and the tensile cuff 74 and a flow path connecting from the pump 14 to the sensing cuff 73, as illustrated in FIG. 5. Additionally, the flow path portion 15 constitutes a flow path connecting from the pressing cuff 71 and the tensile cuff 74 to the atmosphere, and a flow path connecting from the sensing cuff 73 to the atmosphere. The flow path portion 15 is a flow path of air constituted by a hollow portion, a groove, a flow path tank, a tube, or the like provided in the base portion 33 and the like.

The on-off valve 16 opens and closes a portion of the flow path portion 15. Specifically, a plurality of on-off valves 16, specifically four on-off valves 16 are provided, for example, as illustrated in FIG. 5, and selectively open and close the flow path connecting from the pump 14 to the pressing cuff 71 and the tensile cuff 74, the flow path connecting from the pump 14 to the sensing cuff 73, the flow path connecting from the pressing cuff 71 and the tensile cuff 74 to the atmosphere, and the flow path connecting from the sensing cuff 73 to the atmosphere, by the combination of opening and closing of each of the on-off valves 16. As a specific example, the four on-off valves 16 are constituted by the first on-off valve 16A, the second on-off valve 16B, the third on-off valve 16C, and the fourth on-off valve 16D. The first on-off valve 16A opens and closes the flow path connecting the pump 14 and the sensing cuff 73. The second on-off valve 16B opens and closes the flow path connecting the pump 14 and the tensile cuff 74. The second on-off valve 16B and the third on-off valve 16C open and close the flow path connecting the pump 14 and the pressing cuff 71. The second on-off valve 16B, the third on-off valve 16C, and the fourth on-off valve 16D open and close the flow path connecting the pump 14 and the atmosphere.

The pressure sensor 17 at least detects the pressure of the sensing cuff 73. The pressure sensor 17 is provided with the first pressure sensor 17A and the second pressure sensor 17B, for example. The pressure sensor 17 converts a detected pressure into an electrical signal, and outputs the electrical signal to the control substrate 20. For example, the first pressure sensor 17A and the second pressure sensor 17B are provided in the flow path connecting the first on-off valve 16A of the flow path portion 15 and the sensing cuff 73. The flow path is continuous through the pressing cuff 71, the sensing cuff 73, and the tensile cuff 74 to the pump 14 by the opening and closing of each of the on-off valves, and thus the pressure in these flow paths corresponds to the pressure in the internal space of the pressing cuff 71, the sensing cuff 73, and the tensile cuff 74 connecting to the pump 14.

Specifically, for example, the pressure sensor 17 detects the pressure of the sensing cuff 73, i.e., the pressure of the flow path portion 15 connecting the pump 14 and the sensing cuff 73, when the first on-off valve 16A is open and the second on-off valve 16B is closed. Also, the pressure sensor 17 detects the pressure of the sensing cuff 73 and the tensile cuff 74, i.e., the pressure of the flow path portion 15 connecting the pump 14, the sensing cuff 73, and the tensile cuff 74, when the first on-off valve 16A and the second on-off valve 16B are open and the third on-off valve 16C is closed. Furthermore, the pressure sensor 17 detects the pressure of the pressing cuff 71, the sensing cuff 73, and the tensile cuff 74, i.e., the pressure of the flow path portion 15 connecting the pump 14, the pressing cuff 71, the sensing cuff 73, and the tensile cuff 74, when the first on-off valve 16A, the second on-off valve 16B, and the third on-off valve 16C are open and the fourth on-off valve 16D is open or closed.

The power supply unit 18 is, for example, a secondary battery such as a lithium ion battery. The power supply unit 18 is electrically connected to the control substrate 20, as illustrated in FIG. 5. The power supply unit 18 supplies power to the control substrate 20.

As illustrated in FIG. 5, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base portion 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be capable to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 5, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the pressing cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the pressing cuff 71 and the sensing cuff 73 and selectively depressurize the pressing cuff 71 and the sensing cuff 73.

As illustrated in FIGS. 1 to 4, the belt 4 includes a first belt 61 provided on the first pair of lugs 31a and a first spring rod 31b, and a second belt 62 provided on the second pair of lugs 31a and a second spring rod 31b. The belt 4 is wrapped around the wrist 200 with a curler 5 in between.

The first belt 61 is referred to as a so-called a parent and is configured like a band capable of being joined to the second belt 62. As illustrated in FIGS. 1 to 3, the first belt 61 includes a belt portion 61a and a buckle 61b. The belt portion 61a is configured like a band. The belt portion 61a is formed of an elastically deformable resin material. In addition, the belt portion 61a is flexible and includes a sheet-like insert member inside the belt portion 61a for suppressing stretching in the longitudinal direction of the belt portion 61a. The belt portion 61a includes a first hole portion 61c that is formed at one end portion and extends orthogonal to the longitudinal direction of the belt portion 61a, and a second hole portion 61d that is formed at the other end portion and extends orthogonal to the longitudinal direction of the first belt 61.

As illustrated in FIGS. 4 and 6, the first hole portion 61c is provided at the end portion of the belt portion 61a. The first hole portion 61c has an inner diameter at which the spring rod 31b can be inserted into the first hole portion 61c and at which the first belt 61 can rotate with respect to the spring rod 31b. In other words, the first belt 61 is rotatably held by the outer case 31 by disposing the first hole portion 61c between the pair of lugs 31a and around the spring rod 31b.

As illustrated in FIGS. 1 and 3, the second hole portion 61d is provided at the leading end of the belt portion 61a. The buckle 61b is attached to the second hole portion 61d.

As illustrated in FIGS. 1 and 3, the buckle 61b includes a frame body 61e in a rectangular frame shape and a prong 61f rotatably attached to the frame body 61e. A side of the frame body 61e to which the prong 61f is attached is inserted into the second hole portion 61d, and the frame body 61e is mounted rotatably with respect to the belt portion 61a.

The second belt 62 is referred to as a so-called blade tip, and is configured in a band-like shape having a width at which the second belt 62 can be inserted into the frame body 61e. The second belt 62 is formed of an elastically deformable resin material. In addition, the second belt 62 is flexible and includes a sheet-like insert member inside the second belt 62 for suppressing stretching in the longitudinal direction of the second belt 62.

In addition, as illustrated in FIGS. 1 and 2, the second belt 62 includes a plurality of small holes 62a into which the prong 61f is inserted. Additionally, the second belt 62 includes a third hole portion 62b provided at first end portion of the second belt 62 and extending orthogonally to the longitudinal direction of the second belt 62. The third hole portion 62b has an inner diameter at which the spring rod 31b can be inserted into the third hole portion 62b and at which the second belt 62 can rotate with respect to the spring rod 31b. In other words, the second belt 62 is rotatably held by the outer case 31 by disposing the third hole portion 62b between the pair of lugs 31a and around the spring rod 31b.

The second belt 62 is inserted into the frame body 61e, and the prong 61f is inserted into the small hole 62a, and thus the first belt 61 and the second belt 62 are integrally connected together, and the belt 4 as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist of the wearer of the blood pressure measurement device 1.

As illustrated in FIGS. 1 to 4, the curler 5 is configured in a band-like shape that curves in such a manner as to follow along the circumferential direction of the wrist 200. The curler 5 is formed with a first end and a second end spaced apart from each other. For example, a first end side outer surface of the curler 5 is fixed to the rear cover 35 of the device body 3. The curler 5 is disposed at a position where the first end and the second end protrude more to one side of the wrist 200 than the rear cover 35. Accordingly, the curler 5 is disposed with the first end and the second end to one side of the wrist 200 when the blood pressure measurement device 1 is attached to the wrist 200. Furthermore, the first end and the second end of the curler 5 are located adjacent to each other at a predetermined distance from each other. The curler 5 is formed of a resin material, for example. In a specific example, the curler 5 is formed of a polypropylene with a thickness of approximately 1 mm.

In a specific example, as illustrated in FIGS. 1 to 4, the curler 5 is configured in a band-like shape that curves following along the circumferential direction of the wrist. Furthermore, the curler 5 includes the disk-like cover portion 5a provided at a position facing the hand back side of the wrist 200 on the first end side, and constitutes the rear lid together with the rear cover 35, and an escape portion 5b that is provided in the peripheral region of the cover portion 5a and allows the second joining members 35b that fix the outer case 31 and the rear cover 35 to be moveable. For example, the cover portion 5a and the adjacent portion of the cover portion 5a of the curler 5 are formed in a plate-like shape, and the first and second end sides is formed curving with a predetermined curvature more than the cover portion 5a. Furthermore, the length of the curler 5 from the cover portion 5a to the first end is less than the length from the cover portion 5a to the second end. In a specific example, the shorter side of the curler 5 from the cover portion 5a to the first end is disposed on the hand back side of the wrist, and the longer side from the cover portion 5a to the second end extends from the hand back side of the wrist, passing through one side, to the hand palm-side of the wrist 200.

Additionally, as illustrated in FIG. 13, the curler 5 is formed in a shape with the second end located at the inner circumferential surface side of the first end side when the first end and the second end are brought close. In a specific example, the width of the curler 5 in the width direction of the wrist 200 is set to be greater on the hand back side of the wrist 200 than on the hand palm-side of the wrist 200. Furthermore, the radius of curvature of the first end of the curler 5 on the hand back side of the wrist 200 is set to be greater than the radius of curvature of the second end on the hand palm-side of the wrist 200. According to such a configuration, when both end sides of the curler 5 are brought to abut, the second end is disposed further to the inward side of the curler 5 than the first end. Furthermore, the curler 5 is provided with a recess 5c provided adjacent to the cover portion 5a on a portion of the cover portion 5a, on the outer surface on the first end side from the cover portion 5a, and also on the outer surface on the shorter side extending from the cover portion 5a.

The cover portion 5a includes an insert member 5d for reinforcement which is inserted. The cover portion 5a is fixed to the wrist 200 side of the outer case 31 with the fixed rear cover 35 in between. The cover portion 5a includes screw holes 5e provided at positions facing the four hole portions 35c of the rear cover 35, into which the first joining members 35a for fixing the rear cover 35 are screwed, and includes three hole portions 5f for connecting the cuff structure 6 to the device body 3.

The escape portion 5b is a relief for disposing the second joining members 35b in the rear cover 35 and for disposing a tool for rotating the second joining members 35b in a manner so that the second joining members 35b do not interfere with the curler 5 when the rear cover 35 is fixed to the outer case 31 from the rear cover 35 side with the second joining members 35b.

The three hole portions 5f include a first hole portion 5f1 formed with an inner diameter into which a connection portion 84 described below of the pressing cuff 71 can be inserted, a second hole portion 5f2 formed with an inner diameter into which a connection portion 93 described below of the sensing cuff 73 can be inserted, and the third hole portion 5f3 formed with an inner diameter into which the connection portion 103 described below of the tensile cuff 74 can be inserted. In the present embodiment, the second hole portion 5f2 is disposed in the cover portion 5a closer to the second end side on the hand palm-side of the curler 5 than the first hole portion 5f1 and the third hole portion 5f3.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the cuff structure 6 is held by disposing the pressing cuff 71 and the tensile cuff 74 on the inner circumferential surface of the curler 5, and fixing the cuff structure 6 by a joining layer 75 provided between the curler 5 and the pressing cuff 71 and the tensile cuff 74. In the present embodiment, the joining layer 75 is adhesive or double-sided tape.

As illustrated in FIGS. 1 to 6, 14, and 15, the cuff structure 6 includes the pressing cuff 71, a back plate 72, the sensing cuff 73, and the tensile cuff 74. Also, the cuff structure 6 is provided with the joining layer 75 for joining components each other and joining the curler 5 and the cuffs 71 and 74. The cuff structure 6 is fixed to the curler 5. The cuff structure 6 includes the pressing cuff 71, the back plate 72, and the sensing cuff 73 that are stacked one another and disposed on the curler 5, and the tensile cuff 74 that is spaced apart from the pressing cuff 71, the back plate 72, and the sensing cuff 73 and disposed on the curler 5.

In a specific example, as illustrated in FIG. 4, the cuff structure 6 is fixed to the inner circumferential surface of the curler 5 on the hand palm-side of the wrist 200 with the pressing cuff 71, the back plate 72, and the sensing cuff 73 stacked in this order from the inner circumferential surface of the curler 5 toward the wrist 200 side. In addition, the cuff structure 6 includes the tensile cuff 74 disposed on the inner circumferential surface of the curler 5 on the hand back side of the wrist 200. Each of the members of the cuff structure 6 is fixed to an adjacent member of the cuff structure 6 in a stacking direction by the joining layer 75.

The pressing cuff 71 is fluidly connected to the pump 14 through the flow path portion 15. The pressing cuff 71 is inflated to pressing the back plate 72 and the sensing cuff 73 toward the wrist 200 side. As illustrated in FIGS. 9, 10, and 14 to 18, the pressing cuff 71 includes a plurality of, for example, two-layer air bags 81, a target join portion 82 provided on the air bag 81 facing the curler 5, a flow path body (first flow path body) 83 communicating with air bags 81, the connection portion (first connection portion) 84 provided on the leading end of the flow path body 83, and a first thread member 85 provided at least in the flow path body 83. The pressing cuff 71 with such a configuration is configured by integrally welding a plurality of sheet members 86 together.

Here, the air bags 81 are bag-like structures (first bag-like structures), and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. The plurality of air bags 81 are stacked and are in fluid communication with one another in the stacking direction.

Each of the air bags 81 is formed in a rectangular bag-like shape that is long in one direction. Additionally, the air bags 81 are set so that the width in the lateral direction is the same as the width in the lateral direction of the curler 5. The air bags 81 are each constituted by, for example, combining two sheet members 86 and, as illustrated in FIGS. 9, 10, and 14 to 18, welding a weld portion 81a using heat into a rectangular frame shape long in one direction. In addition, the two-layer air bags 81 are constituted by forming with integrally combining two air bags 81 by welding using heat, or with welding together a pair of sheet members 86 facing adjacent air bag 81 and welding to the air bag 81. In a specific example, the two-layer air bags 81 are fluidly continuous through openings provided in the sheet members 86 facing one another. In addition, in the two-layer air bags 81, by bridge welding the opposing sheet members 86 together with a quadrilateral frame shape smaller than the weld portion 81a located on the outer peripheral edge and surrounding the plurality of openings with this bridge weld portion (join portion) 81b, the adjacent air bags 81 are integrally formed and make fluidly continuous on the inner side of the bridge weld portion 81b. Here, bridge in bridge welding and the bridge weld portion 81b means integrally joining adjacent air bags 81.

A single or a plurality of target join portions 82 are provided at at least a portion of the edge portion of the air bag 81 disposed adjacent to the curler 5. The target join portion 82 is formed by a portion of the sheet member 86 forming the air bag 81.

An example of the present embodiment will be described using the examples illustrated in FIGS. 7 to 10 and 14 to 18 in which one target join portion 82 is provided on the edge portion in the lateral direction of each of the air bags 81. Note that, for example, the target join portion 82 may be divided in the longitudinal direction of the air bag 81 by a slit, or a plurality of target join portions 82 may be provided in the longitudinal direction of the air bag 81. The target join portion 82 is at least joined to the outer circumferential surface of the curler 5 when the pressing cuff 71 is disposed on the inner circumferential surface of the curler 5. Furthermore, for example, two target join portions 82 are stacked and welded.

Note that the two target join portions 82 are set to have a different length to the length in the lateral direction of the air bags 81, for example. In this example, the two target join portions 82 are stacked and welded at the first end side in the lateral direction of the curler 5. Note that as long as the two target join portions 82 are able to be disposed with the leading end on the outer circumferential surface of the curler 5, the length is able to be set as appropriate, and the two target join portions 82 may be stackable or not. However, in a case where the length is set to a stackable length, the length is preferably a length such that the leading end does not extend further out than the outer edge of the outer circumferential surface of the curler 5.

As illustrated in FIGS. 7 and 14 to 18, the flow path body 83 is integrally provided on a single air bag 81, for example, on a portion of one edge portion in the longitudinal direction of the air bag 81 adjacent to the curler 5. As a specific example, the flow path body 83 is provided at the end portion of the air bag 81 near the device body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end. The connection portion 84 is, for example, a nipple. As illustrated in in FIGS. 5 and 7, the flow path body 83 is connected to the flow path portion 15 by a third nozzle 34D3 provided on the device body 3 being inserted into the connection portion 84, and constitutes a flow path between the flow path portion 15 of the device body 3 and the air bag 81.

The flow path body 83 is constituted by welding a portion of sheet members 86, which is adjacent to a region of the sheet members 86 constituting the air bags 81, in a frame shape long in one direction using heat, in a state where the connection portion 84 is disposed on the two sheet members 86. The flow path body 83 with such a configuration is disposed between the inner circumferential surface of the curler 5 and the tensile cuff 74, and the leading end is disposed at a position facing the first hole portion 5/1 on the main surface on the wrist 200 side of the region where the cover portion 5a of the curler 5 is provided. In addition, the width of the flow path body 83 not including a weld portion 83a is formed to be 3.8 mm, for example.

Note that, a portion of the weld portion 81a, where the two sheet members 86 are welded in a rectangular frame shape, is not welded and the air bags 81 provided with the flow path body 83 are constituted to be continuous with the weld portion 83a constituting the flow path body 83, and thus the air bags 81 are fluidly continuous with the flow path body 83.

The connection portion 84 has an inner diameter that allows the first thread member 85 to be inserted. The connection portion 84 is provided at the leading end of the flow path body 83. The leading end of the connection portion 84 is exposed from the sheet member 86, facing the curler 5, of the two sheet members 86 constituting the flow path body 83. The connection portion 84 is inserted in the first hole portion 5/1 of the cover portion 5a and is connected to the flow path portion 15.

The first thread member 85 is, for example, a nylon thread formed from a resin material. The first thread member 85 includes two threads 85a, for example. The first thread member 85 is disposed at least in the flow path body 83. Specifically, the first thread member 85 is disposed from the flow path body 83 to the bridge weld portion (join portion) 81b where adjacent bag-like structures 81 are joined together.

The first thread member 85 (the threads 85a) is set with a thread diameter of equal to or less than the sum of the thickness of two sheet members 86. For example, a single sheet member 86 is formed with a thickness of 0.15 mm, and the first thread member 85 is set with a thread diameter of 0.3 mm. Note that the first thread member 85 may not have a circular cross-section, and may have an irregular shape. In the example described above, the thread diameter of the first thread member 85 is two-times the thickness of the sheet members 86 or less. However, variations in the dimensions when fabricating the first thread member 85 and the sheet members 86 are obviously allowed.

As a specific example, as illustrated in FIGS. 9, 10, and 26, the pressing cuff 71 includes a first sheet member 86a, a second sheet member 86b, a third sheet member 86c, and a fourth sheet member 86d in this order from the wrist 200 side. The second sheet member 86b constitutes a first-layer air bag 81 along with the first sheet member 86a, the third sheet member 86c is integrally joined to the second sheet member 86b and constitutes the target join portion 82, and the fourth sheet member 86d constitutes a second-layer air bag 81 and the flow path body 83 along with the third sheet member 86c. Note that the pressing cuff 71 is integrally constituted by joining adjacent sheet members 86 by welding using heat.

The first sheet member 86a and the second sheet member 86b are configured in a similar rectangular shape to the air bags 81, and peripheral edge portions of the four sides are welded to constitute the air bags 81. The second sheet member 86b and the third sheet member 86c are disposed facing each other, and each includes a plurality of openings 86b1 and 86c1 through which the two air bags 81 are fluidly continuous. Additionally, the second sheet member 86b and the third sheet member 86c are integrally joined by the peripheral region of the plurality of openings 86b1 and 86c1 being welded using heat in a quadrilateral frame shape smaller than the welded four sides of the air bags 81.

The third sheet member 86c, for example, is constituted in a shape that allows the air bags 81, the target join portion 82, and the flow path body 83 to be constituted. The fourth sheet member 86d, for example, is constituted in a shape that allows the air bags 81 and the flow path body 83 to be constituted. Furthermore, the fourth sheet member 86d includes a hole portion 86d1 into which the leading end of the connection portion 84 can be inserted, for example.

The air bags 81, the target join portion 82, and the flow path body 83 are constituted by the third sheet member 86c and the fourth sheet member 86d being disposed facing one another, welded using heat along the peripheral edge shape of the air bag 81 and the flow path body 83 so that the air bag 81 and the flow path body 83 are fluidly continuous, and cut in a predetermined shape.

The hole portion 86d1 of the fourth sheet member 86d is disposed with the connection portion 84, and the peripheral region of the hole portion 86d1 is welded to the connection portion 84 using heat. After the bag-like structure 81, the target join portion 82, the flow path body 83, and the connection portion 84 are integrally formed, the two nylon threads, i.e., the first thread member 85, are inserted from the connection portion 84. Furthermore, the fourth sheet member 86d is joined with the inner circumferential surface of the curler 5 with the joining layer 75 in between, and the target join portion 82 of the third sheet member 86c is joined to the outer circumferential surface of the curler 5 with the joining layer 75 in between.

As illustrated in FIGS. 9, 10, and 26, the back plate 72 is applied to the outer surface of the first sheet member 86a of the pressing cuff 71 by the joining layer 75. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72. Here, the contact as used herein includes both direct contact and indirect contact with the sensing cuff 73 in between.

For example, as illustrated in FIG. 10, the back plate 72 includes a plurality of grooves 72a extending in both main surfaces of the back plate 72 in a direction orthogonal to the longitudinal direction. The plurality of grooves 72a face the corresponding grooves 72a provided in the other main surface in the thickness direction of the back plate 72. Additionally, the plurality of grooves 72a are disposed at equal intervals in the longitudinal direction of the back plate 72.

In the back plate 72, portions including the plurality of grooves 72a are thinner than portions including no grooves 72a and thus the portions including the plurality of grooves 72a are easily deformed. Accordingly, the back plate 72 is deformed in such a manner as to follow to the shape of the wrist 200, and has shape followability of extending in the circumferential direction of the wrist. The back plate 72 is formed such that the length of the back plate 72 is sufficient to cover the hand palm-side of the wrist 200. The back plate 72 transfers the pressing force from the pressing cuff 71 to the back plate 72 side main surface of the sensing cuff 73 in a state in which the back plate 72 is extending along the shape of the wrist 200.

The sensing cuff 73 is fluidly connected to the pump 14 through the flow path portion 15. The sensing cuff 73 is fixed to the main surface of the back plate 72 on the wrist 200 side. The sensing cuff 73 is in direct contact with a region of the wrist 200 where an artery 210 resides, as illustrated in FIGS. 4 and 26. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated pressing cuff 71 toward the wrist 200 side with the back plate 72 in between.

In a specific example, as illustrated in FIGS. 9, 10, and 19 to 21, the sensing cuff 73 includes one air bag 91, a flow path body (second flow path body) 92 that communicates with the air bag 91, the connection portion 93 provided at the leading end of the flow path body 92, and a second thread member 94 provided at least in the flow path body 92. One main surface of the air bag 91 of the sensing cuff 73 is fixed to the back plate 72. For example, the sensing cuff 73 is joined to the main surface of the back plate 72 on the wrist 200 side by the joining layer 75. The sensing cuff 73 with such a configuration is constituted by welding two sheet members 96.

Here, the air bag 91 is a bag-like structure (second bag-like structure), and in the present embodiment, the blood pressure measurement device 1 is configured to use air with the pump 14, and thus the present embodiment will be described using the air bag. However, in a case where a fluid other than air is used, the bag-like structure may be a liquid bag and the like.

The air bag 91 is constituted in a rectangular shape that is long in one direction. The air bags 91 are each constituted by, for example, combining two sheet members 96 long in one direction and, as illustrated in FIGS. 9, 10, 14, 15, and 19 to 21, welding a weld portion 91a using heat into a rectangular frame shape long in one direction. Also, the air bag 91, for example, includes a junction margin 91b for ensuring area for joining the air bag 91 to the back plate 72 using the joining layer 75. The junction margin 91b is formed by the sheet member 96 facing the back plate 72, for example.

The flow path body 92 is integrally provided at a portion of one edge portion of the air bag 91 in the longitudinal direction. As a specific example, the flow path body 92 is provided at the end portion of the air bag 91 near the device body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The connection portion 93 is, for example, a nipple. As illustrated in in FIGS. 5 and 7, the flow path body 92 is connected to the flow path portion 15 by a first nozzle 34D1 provided on the device body 3 being inserted into the connection portion 93, and constitutes a flow path between the flow path portion 15 of the device body 3 and the air bag 91.

The flow path body 92 is constituted by welding a portion of sheet members 96, which is adjacent to a region of the sheet members 96 constituting the air bag 91, in a frame shape long in one direction using heat, in a state where the connection portion 93 is disposed on the two sheet members 96. Note that, a portion of the weld portion 91a, where the two sheet members 96 are welded in a rectangular frame shape, is not welded and the air bag 91 is constituted to be continuous with the weld portion 92a constituting the flow path body 92, and thus the air bag 91 and the flow path body 92 are fluidly continuous. The flow path body 92 with such a configuration is disposed between the inner circumferential surface of the curler 5 and the tensile cuff 74, and the leading end is disposed at a position facing the second hole portion 5f2 on the main surface on the wrist 200 side of the region where the cover portion 5a of the curler 5 is provided. In addition, the width of the flow path body 92 not including the weld portion 92a is 3.8 mm, for example.

The connection portion 93 has an inner diameter that allows the second thread member 94 to be inserted. The connection portion 93 is provided at the leading end of the flow path body 92. Also, the leading end of the connection portion 93 is externally exposed from the sheet member 96 facing the curler 5 and the back plate 72, of the two sheet members 96 constituting the flow path body 92. The connection portion 93 is inserted in the second hole portion 5f2 of the cover portion 5a and is connected to the flow path portion 15.

The second thread member 94 is, for example, a nylon thread formed from a resin material. For example, the number and length of the second thread member 94 may be different from that of the first thread member 85. The second thread member 94 includes three threads, for example. In a specific example, the second thread member 94 includes two first threads 94a formed in the same length and one second thread 94b that is longer than the first threads 94a. The first threads 94a are disposed in the flow path body 92. The second thread 94*b* is disposed from the flow path body 92 to an end portion on the opposite side to where the flow path body 92 of the air bag 91 is provided.

In a similar manner to the first thread member 85, the second thread member 94 (the first threads 94*a* and the second thread 94*b*) is set with a thread diameter of equal to or less than the sum of the thickness of two sheet members 96. For example, a single sheet member 96 is formed with a thickness of 0.15 mm, and the second thread member 94 is set with a thread diameter of 0.3 mm. Note that the second thread member 94 may not have a circular cross-section, and may have an irregular shape. In the example described above, the thread diameter of the second thread member 94 is two-times the thickness of the sheet members 96 or less. However, variations in the dimensions when fabricating the second thread member 94 and the sheet members 96 are obviously allowed.

In a specific example, the sensing cuff 73 includes a fifth sheet member 96*a* and a sixth sheet member 96*b* in this order from the wrist 200 side as illustrated in FIGS. 9 and 10. Note that the sensing cuff 73 is constituted by joining adjacent sheet members 96 by welding using heat.

For example, the fifth sheet member 96*a* and the sixth sheet member 96*b* are constituted in a shape that allows the air bag 91, the junction margin 91*b*, and the flow path body 92 to be constituted. The air bag 91 and the flow path body 92 are constituted by the fifth sheet member 96*a* and the sixth sheet member 96*b* being disposed facing one another, welded using heat along the peripheral edge shape of the air bag 91 and the flow path body 92 so that the air bag 91 and the flow path body 92 are fluidly continuous, and cut in a predetermined shape.

Furthermore, the sixth sheet member 96*b* includes a hole portion 96*b*1 into which the leading end of the connection portion 93 can be inserted, for example. The connection portion 93 is disposed in the hole portion 96*b*1, and the peripheral region of the hole portion 96*b*1 is welded to the connection portion 93 using heat. After the bag-like structure 91, the flow path body 92, and the connection portion 93 are integrally formed, the two first threads 94*a* and the second thread 94*b*, i.e., the second thread member 94, are inserted from the connection portion 93. The sixth sheet member 96*b* is joined to the inner circumferential surface of the back plate 72 with the joining layer 75 in between.

The tensile cuff 74 is fluidly connected to the pump 14 through the flow path portion 15. The tensile cuff 74 is inflated to press the curler 5 such that the curler 5 is spaced apart from the wrist 200, pulling the belt 4 and the curler 5 toward the hand back side of the wrist 200. The tensile cuff 74 includes a plurality of, for example, six-layer air bags 101, a target join portion 102 provided on the air bag 101 facing the curler 5, the connection portion (third connection portion) 103 provided on the air bag 101 facing the curler 5, and a cutout portion 104 provided on at least the air bag 101 facing the curler 5. The tensile cuff 74 with such a configuration is constituted by welding a plurality of sheet members 106. In addition, the tensile cuff 74 is fixed to the region where the flow path bodies 83 and 92 are provided and the curler 5, including the cover portion 5*a*, on the hand back side of the wrist 200. In other words, the flow path body 83 of the pressing cuff 71 and the flow path body 92 of the sensing cuff 73 are disposed between the curler 5 on the hand back side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71 in the inflating direction during inflation and than the thickness of the sensing cuff 73 in the inflating direction during inflation. Specifically, the air bags 101 of the tensile cuff 74 include more layer structures than the air bags 81 in the pressing cuff 71 and the air bag 91 in the sensing cuff 73, and have thicker thickness than the pressing cuff 71 and the sensing cuff 73 when the air bags 101 are inflated from the curler 5 toward the wrist 200.

In the present embodiment, the tensile cuff 74 including the six-layer air bags 101 includes a first outer layer 111 constituted by one air bag 101, a first intermediate layer 112 constituted by two air bags 101 integrally combining with the first outer layer 111 by welding using heat, a second intermediate layer 113 constituted by two-layer air bags 101 integrally combining with the first intermediate layer 112 by welding using heat, and a second outer layer 114 constituted by one air bag 101 integrally combining with the second intermediate layer 113 by welding using heat.

Here, the air bags 101 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. A plurality of the air bags 101 are stacked and are in fluid communication in the stacking direction.

Each of the air bags 101 is formed in a rectangular bag-like shape that is long in one direction. Additionally, the air bags 101 are set so that the width in the lateral direction is the same as the width in the lateral direction of the curler 5. The air bags 101 are each constituted by, for example, combining two sheet members 106 and, as illustrated in FIGS. 11, 12, 14, and 15, welding a weld portion 101*a* using heat into a rectangular frame shape long in one direction. The six-layer air bags 101 are fluidly continuous through openings provided in the sheet members 106 facing one another.

In addition, in the six-layer air bags 101, for the first outer layer 111 and the first intermediate layer 112, the first intermediate layer 112 and the second intermediate layer 113, and the second intermediate layer 113 and the second outer layer 114, by bridge welding the opposing sheet members 106 together with a quadrilateral frame shape smaller than the weld portion 81*a* located on the outer peripheral edge, and surrounding the plurality of openings with the bridge weld portion (join portion) 101*b*, the adjacent air bags 101 are integrally formed and made fluidly continuous on the inner side of the bridge weld portion 101*b*.

The first outer layer 111 is formed by one air bag 101 disposed on the wrist 200 side. The first outer layer 111 constitutes the first air bag 101 of the six-layer air bags 101 from the wrist 200 side.

The first intermediate layer 112 is stacked on the first outer layer 111. The first intermediate layer 112 is formed by two-layer air bags 101. The first intermediate layer 112 constitutes the second and third air bag 101 of the six-layer air bags 101 from the wrist 200 side. The first intermediate layer 112 is constituted by two-layer air bags 101 integrally welded at the outer peripheral edge. In other words, the first intermediate layer 112 is formed by integrally welding four sheet members 106 in the outer peripheral edge shape of the air bags 101.

The second intermediate layer 113 is stacked on the first intermediate layer 112. The second intermediate layer 113 is formed by two-layer air bags 101. The second intermediate layer 113 constitutes the fourth and fifth air bag 101 of the six-layer air bags 101 from the wrist 200 side. The second intermediate layer 113 is constituted by two-layer air bags 101 integrally welded at the outer peripheral edge. In other words, the second intermediate layer 113 is formed by integrally welding four sheet members 106 in the outer peripheral edge shape of the air bags 101.

The second outer layer 114 is formed by one air bag 101 disposed on the curler 5 side. The second outer layer 114 constitutes the sixth air bag 101 of the six-layer air bags 101 from the wrist 200 side.

A single or a plurality of target join portions 102 are provided at at least a portion of the edge portion of the air bag (the sixth air bag) 101 disposed adjacent to the curler 5. The target join portion 102 is formed by a portion of the sheet member 106 forming the air bag 101.

An example of the present embodiment will be described using examples in which two target join portions 102 are each provided in the longitudinal direction of the air bags 101 on the edge portion in the lateral direction of each of the air bags 101. Note that, for example, the target join portions 102 are provided on the air bags 101 avoiding the positions facing the cover portion 5a of the curler 5. Furthermore, for example, the target join portion 102 includes an escape portion 102a, which is for externally exposing a power feeding terminal 8b described below of the power feeding unit 8 provided on the curler 5, at a portion facing the power feeding terminal 8b. The escape portion 102a, for example, is an opening through which the power feeding terminal 8b can be externally exposed and has a circular shape as an example.

The target join portion 102 is at least joined to the outer circumferential surface of the curler 5 when the tensile cuff 74 is disposed on the inner circumferential surface of the curler 5. Additionally, the target join portions 102 disposed at the same position in the lateral direction of the air bags 101 are stacked and welded.

Note that the two target join portions 102 are set to have a different length to the length in the lateral direction of the air bags 101, for example. In this example, the two target join portions 102 are stacked and welded at the first end side in the lateral direction of the curler 5. Note that as long as the two target join portions 102 are able to be disposed with the leading end on the outer circumferential surface of the curler 5, the length is able to be set as appropriate and the two target join portions 102 may be stackable or not. However, in a case where the length is set to a stackable length, the length is preferably a length such that the leading end does not extend further out than the outer edge of the outer circumferential surface of the curler 5.

The connection portion 103 is, for example, a nipple. The connection portion 103 is provided at a position facing the third hole portion 5f3 of the cover portion 5a in a central region in the longitudinal direction of the air bag 101 disposed adjacent to the curler 5. The leading end of the connection portion 103 is exposed from the sheet member 106 facing the curler 5, of the two sheet members 106 forming the air bag 101. As illustrated in FIGS. 5 and 7, the connection portion 103 is connected to the flow path portion 15 by being connected to the second nozzle 34D2 provided on the device body 3.

The cutout portion 104 is provided at a position facing the escape portion 5b provided on the curler 5. The cutout portion 104 is provided on the sixth air bag 101 forming the second outer layer 114.

In a specific example, as illustrated in FIGS. 11 and 12, the tensile cuff 74 includes a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k, and an eighteenth sheet member 106l in this order from the wrist 200 side. Note that the tensile cuff 74 is integrally constituted by joining adjacent sheet members 106 by welding using heat.

The seventh sheet member 106a to the eighteenth sheet member 106l are constituted in a similar rectangular shape to the air bags 101. The seventh sheet member 106a and the eighth sheet member 106b are welded using heat along the peripheral edge portion shape on the four sides of the air bags 101 to constitute the first (first layer) air bag 101 from the wrist 200 side. In other words, the seventh sheet member 106a and the eighth sheet member 106b constitute the first outer layer 111.

The eighth sheet member 106b and the ninth sheet member 106c are disposed facing each other, and each includes a plurality of openings 106b1 and 106c1 through which the two air bags 101 are fluidly continuous. Additionally, the eighth sheet member 106b and the ninth sheet member 106c are integrally joined by the peripheral region of the plurality of openings 106b1 and 106c1 being bridge welded using heat in a quadrilateral frame shape smaller than the welded four sides of the air bags 101.

The ninth sheet member 106c and the tenth sheet member 106d are welded using heat along the peripheral edge portion shape on the four sides of the air bags 101 to constitute the second (second layer) air bag 101 from the wrist 200 side.

As illustrated in FIGS. 11 and 12, the tenth sheet member 106d and the eleventh sheet member 106e include a plurality of openings 106d1 and 106e1 disposed facing one another and through which the two air bags 101 are fluidly continuous. The eleventh sheet member 106e and the twelfth sheet member 106f are welded using heat along the peripheral edge portion shape on the four sides of the air bags 101 to constitute the third (third layer) air bag 101 from the wrist 200 side.

The ninth sheet member 106c, the tenth sheet member 106d, the eleventh sheet member 106e, and the twelfth sheet member 106f are integrally welded using heat along the peripheral edge portion shape on the four sides of the air bags 101 to constitute the first intermediate layer 112 in which the second and third air bags 101 are integrally formed.

As illustrated in FIGS. 11 and 12, the twelfth sheet member 106f and the thirteenth sheet member 106g include a plurality of openings 106f1 and 106g1 disposed facing one another and through which the two air bags 101 are fluidly continuous. Additionally, the twelfth sheet member 106f and the thirteenth sheet member 106g are integrally joined by the peripheral region of the plurality of openings 106f1 and 106g1 being bridge welded using heat in a quadrilateral frame shape smaller than the welded four sides of the air bags 101.

The thirteenth sheet member 106g and the fourteenth sheet member 106h are welded using heat along the peripheral edge portion shape on the four sides of the air bags 101 to constituted the fourth (fourth layer) air bag 101 from the wrist 200 side.

As illustrated in FIGS. 11 and 12, the fourteenth sheet member 106h and the fifteenth sheet member 106i include a plurality of openings 106h1 and 10611 disposed facing one another and through which the two air bags 101 are fluidly continuous. The fifteenth sheet member 106i and the sixteenth sheet member 106*j* are welded using heat along the peripheral edge portion shape on the four sides of the air bags 101 to constituted the fifth (fifth layer) air bag 101 from the wrist 200 side.

The thirteenth sheet member 106*g*, the fourteenth sheet member 106*h*, the fifteenth sheet member 106*i*, and the sixteenth sheet member 106*j* are integrally welded using heat along the peripheral edge portion shape on the four sides of the air bags 101 to constitute the second intermediate layer 113 in which the fourth and fifth air bags 101 are integrally formed.

As illustrated in FIGS. 11 and 12, the sixteenth sheet member 106*j* and the seventeenth sheet member 106*k* include a plurality of openings 106*j*1 and 106*k*1 disposed facing one another and through which the two air bags 101 are fluidly continuous. Also, the seventeenth sheet member 106*k*, for example, is constituted in a shape that allows the air bag 101 and the target join portion 102 to be constituted. Additionally, the sixteenth sheet member 106*j* and the seventeenth sheet member 106*k* are integrally joined by the peripheral region of the plurality of openings 106*j*1 and 106*kl* being bridge welded using heat in a quadrilateral frame shape smaller than the welded four sides of the air bags 101.

The seventeenth sheet member 106*k* and the eighteenth sheet member 106*l* are welded using heat along the peripheral edge portion shape on the four sides of the air bag 101 and cut in a predetermined shape to constitute the sixth air bag 101 from the wrist 200 side, which includes the cutout portion 104, and the target join portion 102.

Furthermore, the eighteenth sheet member 106*l* includes a hole portion 106*l*1 into which the leading end of the connection portion 103 can be inserted, for example. The eighteenth sheet member 106*l* is disposed with the connection portion 103 at the hole portion 106*l*1, and the peripheral region of the hole portion 106*l*1 is welded to the connection portion 103 using heat. Furthermore, the eighteenth sheet member 106*l* is joined with the inner circumferential surface of the curler 5 with the joining layer 75 in between, and the target join portion 102 of the seventeenth sheet member 106*k* is joined to the outer circumferential surface of the curler 5 with the joining layer 75 in between.

Additionally, each of the sheet members 86, 96, and 106 forming the pressing cuff 71, the sensing cuff 73, and the tensile cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin. Note that, in the pressing cuff 71 and the sensing cuff 73, of at least the plurality of sheet members 86 and 106 constituting the air bags 81 and 101, at least the sheet members 86 and 106 welded to the curler 5 are constituted by a material similar to the material of the curler 5.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path portion 15, the on-off valves 16, the pressure sensors 17, the pressing cuff 71, the sensing cuff 73, and the tensile cuff 74. A specific example of the fluid circuit 7 will be described below.

As illustrated in FIG. 5, for example, the fluid circuit 7 includes a first flow path 7*a* in which the pump 14, the sensing cuff 73, the first pressure sensor 17A and the second pressure sensor 17B are continuous through the first on-off valve 16A, a second flow path 7*b* which is constituted by branching from the first flow path 7*a* between the pump 14 and the first on-off valve 16A and is continuous from the pump 14 to the atmosphere through the second on-off valve 16B, the third on-off valve 16C, and the fourth on-off valve 16D sequentially in this order, a third flow path 7*c* which is constituted by branching from an intermediate portion of the second flow path 7*b* between the second on-off valve 16B and the third on-off valve 16C and is continuous from the pump 14 to the tensile cuff 74, and a fourth flow path 7*d* which is constituted by branching from an intermediate portion of the second flow path 7*b* between the third on-off valve 16C and the fourth on-off valve 16D and is continuous from the pump 14 to the pressing cuff 71.

In the fluid circuit 7 with such a configuration, by the second on-off valve 16B and the third on-off valve 16C being open and the first on-off valve 16A and the fourth on-off valve 16D being closed, the third flow path 7*c* and the fourth flow path 7*d* branching from the second flow path 7*b* are connected to the pump 14, and the pump 14, the pressing cuff 71, and the tensile cuff 74 are fluidly connected.

In the fluid circuit 7, by the first on-off valve 16A, the second on-off valve 16B, and the third on-off valve 16C being open and the fourth on-off valve 16D being closed, the first flow path 7*a* and the third flow path 7*c* and the fourth flow path 7*d* branching from the second flow path 7*b* are connected to the pump 14, and the pump 14, the pressing cuff 71, and the tensile cuff 74 and the pump 14 and the sensing cuff 73 are fluidly connected. In the fluid circuit 7, by the second on-off valve 16B, the third on-off valve 16C, and the fourth on-off valve 16D being open and the first on-off valve 16A being closed, the second flow path 7*b*, the third flow path 7*c*, and the fourth flow path 7*d* are connected to the pump 14, and the pump 14, the pressing cuff 71, the tensile cuff 74, and the atmosphere are fluidly connected. In the fluid circuit 7, by the first on-off valve 16A, the second on-off valve 16B, the third on-off valve 16C, and the fourth on-off valve 16D being open, the first flow path 7*a*, the second flow path 7*b*, the third flow path 7*c*, and the fourth flow path 7*d* are connected to the pump 14, and the pump 14, the pressing cuff 71, the sensing cuff 73, the tensile cuff 74, and the atmosphere are fluidly connected.

As illustrated in FIGS. 6 and 8, the power feeding unit 8 is provided in the recess 5*c* formed in the outer surface of the curler 5 on the first end side that projects from the device body 3. For example, the power feeding unit 8 is configured to be capable to connect to a connector provided on a charging cable of a charger.

As illustrated in FIGS. 3, 6, and 8, the power feeding unit 8 is provided with a wiring portion 8*a*, the power feeding terminal 8*b*, and a cover 8*c* that covers the wiring portion 8*a* disposed in the recess 5*c* of the curler 5. The first end of the wiring portion 8*a* is connected to the power feeding terminal 8*b*, and the second end is connected to the control unit 55. The power feeding terminal 8*b* is constituted by two circular terminals, for example. For example, the wiring portion 8*a* and the power feeding terminal 8*b* are formed of flexible printed circuits (FPC) and the like including a base film, such as polyimide, provided with an electrically conductive metal film and the like. The cover 8*c* is formed in the same shape as the recess 5*c* and covering the recess 5*c*, and the upper surface runs flush with the outer surface of the curler 5 on the shorter side when the cover 8*c* is provided in the recess 5*c*.

Next, an example of measurement of a blood pressure value using the blood pressure measurement device 1 will be described using FIGS. 22 to 25. FIG. 22 is a flowchart illustrating an example of blood pressure measurement using the blood pressure measurement device 1 which is illustrating both of the operations of a user and the operations of the control unit 55. Additionally, FIGS. 23 to 25 illustrate an example in which the blood pressure measurement device 1 is attached to the wrist 200 of the user.

First, the user attaches the blood pressure measurement device 1 to the wrist 200 (step ST11). In a specific example, for example, the user inserts one of the wrists 200 into the curler 5, as illustrated in FIG. 23.

At this time, in the blood pressure measurement device 1, the device body 3 and the sensing cuff 73 are disposed at opposite positions in the curler 5, and thus the sensing cuff 73 is disposed in a region on the hand palm-side of the wrist 200 in which the artery 210 resides. Thus, the device body 3 and the tensile cuff 74 are disposed on the hand back side of the wrist 200. Then, as illustrated in FIG. 24, the user passes the second belt 62 through the frame body 61*e* of the buckle 61*b* of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61*f* into one of the small holes 62*a*. Thus, as illustrated in FIGS. 4 and 25, the first belt 61 and the second belt 62 are connected, and the blood pressure measurement device 1 is attached to the wrist 200.

Next, the user operates the operation unit 13 and inputs an instruction corresponding to starting measurement of blood pressure value. The operation unit 13 on which the instruction input operation was performed outputs an electrical signal corresponding to starting measurement to the control unit 55 (step ST12). The control unit 55, when the electrical signal is received, for example, opens the first on-off valve 16A, the second on-off valve 16B, and the third on-off valve 16C, closes the fourth on-off valve 16D, and operates the pump 14 to supply compressed air to the pressing cuff 71, the sensing cuff 73, and the tensile cuff 74 through the first flow path 7*a*, the second flow path 7*b*, the third flow path 7*c*, and the fourth flow path 7*d* (step ST13). Thus, the pressing cuff 71, the sensing cuff 73, and the tensile cuff 74 start to be inflated.

The first pressure sensor 17A and the second pressure sensor 17B detect the pressures in the pressing cuff 71, the sensing cuff 73, and the tensile cuff 74, and output, to the control unit 55, electrical signals corresponding to the pressures (step ST14). On the basis of the received electrical signals, the control unit 55 determines whether the pressures in the internal spaces of the pressing cuff 71, the sensing cuff 73, and the tensile cuff 74 have reached a predetermined pressure for measurement of the blood pressure (step ST15). For example, in a case where the internal pressures of the pressing cuff 71 and the tensile cuff 74 have not reached the predetermined pressure and the internal pressure of the sensing cuff 73 has reached the predetermined pressure, the control unit 55 closes the first on-off valve 16A and supplies the compressed air through the second flow path 7*b*, the third flow path 7*c*, and the fourth flow path 7*d*.

When the internal pressures of the pressing cuff 71 and the tensile cuff 74 and the internal pressure of the sensing cuff 73 all have reached the predetermined pressure, the control unit 55 stops driving the pump 14 (YES in step ST15). At this time, as illustrated by the two-dot chain line in FIG. 4, the pressing cuff 71 and the tensile cuff 74 are sufficiently inflated, and the inflated pressing cuff 71 presses the back plate 72. Additionally, the tensile cuff 74 presses against the curler 5 in a direction away from the wrist 200, and then the belt 4, the curler 5, and the device body 3 move in a direction away from the wrist 200, and as a result, the pressing cuff 71, the back plate 72, and the sensing cuff 73 are pulled toward the wrist 200 side. In addition, when the belt 4, the curler 5, and the device body 3 move in a direction away from the wrist 200 due to the inflation of the tensile cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Furthermore, the sensing cuff 73 is inflated by being supplied with a predetermined amount of air such that the internal pressure equals the pressure required to measure blood pressure, and is pressed toward the wrist 200 by the back plate 72 that is pressed by the pressing cuff 71. Thus, the sensing cuff 73 presses the artery 210 in the wrist 200 and occludes the artery 210 as illustrated in FIG. 26.

Additionally, the control unit 55, for example, controls the third on-off valve 16C and repeats the opening and closing of the third on-off valve 16C, or adjusts the degree of opening of the third on-off valve 16C to pressurize a pressure of the internal space of the pressing cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST16). The control unit 55 outputs an image signal corresponding to the obtained measurement results to the display unit 12, and displays the measurement results on the display unit 12 (step ST17). In addition, after the end of the blood pressure measurement, the control unit 55 opens the first on-off valve 16A, the second on-off valve 16B, the third on-off valve 16C, and the fourth on-off valve 16D.

The display unit 12 receives the image signal, and then displays the measurement results on the screen. The user views the display unit 12 to confirm the measurement results. After the measurement is complete, the user removes the prong 61*f* from the small hole 62*a*, removes the second belt 62 from the frame body 61*e*, and pulls out the wrist 200 from the curler 5, thus detaching the blood pressure measurement device 1 from the wrist 200.

The blood pressure measurement device 1 according to an embodiment with such a configuration has a configuration in which the tensile cuff 74 is disposed on the back of the hand (cover portion 5*a*) side, where the device body 3 is provided, of the curler 5 provided around the wrist 200, and the pressing cuff 71 and the sensing cuff 73 are disposed on the hand palm-side. In addition, the blood pressure measurement device 1 has a configuration in which the air bags 81 of the pressing cuff 71 are connected to the flow path portion 15 through the flow path body 83, and the air bag 91 of the sensing cuff 73 is connected to the flow path portion 15 through the flow path body 92. Furthermore, the flow path bodies 83 and 92 are configured by welding the two sheet members 86 and 96, respectively.

Thus, the thickness of the flow path bodies 83 and 92 correspond to the thickness of the two sheet members 86 and 96, respectively. Thus, even in a case where the flow path bodies 83 and 92 are disposed between the tensile cuff 74 and the curler 5, the flow path bodies 83 and 92 are prevented from affecting on the expansion of the tensile cuff 74. In addition, because the flow path bodies 83 and 92 are constituted by joining the two sheet members 86 and 96, deformation of the flow path bodies 83 and 92 in the thickness direction thereof is suppressed, and the flow path bodies 83 and 92 are suppressed from closing due to the expansion of the tensile cuff 74.

In addition, because the flow path bodies 83 and 92 are disposed between the curler 5 and the tensile cuff 74, the flow path bodies 83 and 92 can be prevented as much as possible from being exposed to the outside. Thus, the blood pressure measurement device 1 can be made smaller in size and design can be improved. Furthermore, because the connection portions 84 and 93 are pressed to the device body 3 side by the tensile cuff 74, the connection portions 84 and 93 can be prevented from detaching from the flow path portion 15.

In addition, because the pressing cuff 71 and the sensing cuff 73 include the thread members 85 and 94, respectively, at least provided in the flow path bodies 83 and 92, a gap is formed by the thread members 85 and 94 between the two sheet members 86 and 96 forming the flow path bodies 83 and 92, respectively. Thus, even in a case where the flow path bodies 83 and 92 are pressed by the wrist 200 when the tensile cuff 74 is inflated or the blood pressure measurement device 1 is attached on the wrist 200, as illustrated in FIGS. 18 and 21, a gap is formed by the thread members 85 and 94 between the two sheet members 86 and 96, respectively. Thus, with the blood pressure measurement device 1, the flow path bodies 83 and 92 can be prevented from being closed by the thread members 85 and 94.

In other words, in the blood pressure measurement device 1, by providing the thread members 85 and 94 in the flow path bodies 83 and 92, a gap that constitutes a flow path from the connection portions 84 and 93 to the air bags 81 and 91 can be ensured. Thus, air can be reliably supplied to the bag-like structures 81 and 91. This allows the blood pressure measurement device 1 to perform a suitable blood pressure measurement.

In addition, because the first thread member 85 includes two thread disposed at least in the flow path body 83, even in a case where the sheet members 86 are pressed by an external force in a direction pressing them tightly together, a gap is formed between the adjacent threads 85. Thus, with the blood pressure measurement device 1, the pressing cuff 71 can be suitably inflated.

In addition, the two-layer air bags 81 are welded (joined) in a rectangular frame-like shape at inside from the weld portion 81a of the peripheral edge portion, which is the outer peripheral edge of the air bags 81, and are fluidly continuous through the opening 86c1 and 86b1 at inside from the bridge weld portion 81b that is bridge welded. The first thread member 85 is disposed from the flow path body 83 to the bridge weld portion 81b. Thus, air can be reliably supplied to the opening that fluidly connects the air bags 81 together, allowing the two-layer air bags 81 to be suitably inflated.

The second thread member 94 provided in the sensing cuff 73 includes the first threads 94a disposed in the flow path body 92 and the second thread 94b, which is formed to be longer than the first threads 94a, disposed in the air bag 91 and the flow path body 92. Thus, the first threads 94a and the second thread 94b in the flow path body 92 and the second thread 94b in the air bag 91 form a gap between the sheet members 86. Thus, with the blood pressure measurement device 1, the sensing cuff 73 can be reliably and suitably inflated, and more suitable blood pressure measurement can be performed.

Additionally, because the second thread member 94 includes the two first threads 94a and the one second thread 94b, the two first threads 94a and the one second thread 94b are disposed in the flow path body 92, and the one second thread 94b is disposed in the air bag 91. Thus, even in a case where the sheet members 96 are pressed by an external force in a direction pressed them tightly together, a gap can be reliably formed between adjacent threads on the flow path body 92.

In addition, the three threads 94a, 94b are disposed in the flow path body 92, and thus the volume of the flow path body 92 can be reduced. And only the one thread 94b is disposed on the air bag 91, and thus the reduction of volume of the air bag 91 is prevented as much as possible. Thus, with the blood pressure measurement device 1, the sensing cuff 73 can be suitably inflated and the accuracy of the blood pressure measurement can be improved.

Furthermore, the first thread member 85 and the second thread member 94 use a thread with a thread diameter set to the sum of the thickness of the two sheet members or less. Thus, the surface of the pressing cuff 71 and the sensing cuff 73 can be prevented from bulging due to the first thread member 85 and the second thread member 94. Also, in a case where the sensing cuff 73, with which blood pressure measurement is performed, is configured to come into close contact with the wrist, a reduction in the tactile sensation of the sensing cuff 73 can be prevented and the wrist 200 being compressed by the second thread 94b of the second thread member 94 can be prevented.

In addition, the connection portions 84 and 93 are constituted as nipples with an inner diameter that allows the first thread member 85 and the second thread member 94 to be inserted, and the first thread member 85 and the second thread member 94 are constituted as separate members to the sheet members 86 and 96. With this configuration, because the first thread member 85 and the second thread member 94 can be inserted in the flow path bodies 83 and 92 from the nipples, manufacturing the pressing cuff 71 and the sensing cuff 73 is made easier. In addition, because the pressing cuff 71 and the sensing cuff 73 are disposed curving to the inner circumferential surface of the curler 5, a difference is formed between the inner and outer circumference of the two sheet members 86 and 96, and the first thread member 85 and the second thread member 94 are sandwiched and held by the two sheet members 86 and 96. Therefore, even in a case where the first thread member 85 and the second thread member 94 are not also fixed after being inserted in the flow path bodies 83 and 92, respectively, the first thread member 85 and the second thread member 94 moving inside the flow path bodies 83 and 92 and the air bags 81 and 91 can be suppressed.

As described above, according to the blood pressure measurement device 1 of the present embodiment with a configuration such as that described above, the cuff can be suitably inflated.

Note that the present invention is not limited to the embodiments described above. In the example described above, the first thread member 85 is disposed from the flow path body 83 to the bridge weld portion 81b of the air bags 81, the second thread member 94 includes the first thread 94a disposed in the flow path body 92 and the second thread 94b disposed in the flow path body 92 and the air bag 91, as an example. However, no such limitation is intended. In other words, by disposing the first thread member 85 and the second thread member 94 at least in the flow path bodies 83 and 92, the flow path bodies 83 and 92 can be prevented from being closed, and thus air can be reliably supplied to the air bags 81 and 91. For example, the thread member 94 may be configured to be provided in only the sensing cuff 73.

In the example described above, the configuration has been described in which the first thread member 85 and the second thread member 94 are inserted into the flow path bodies 83 and 92. However, no such limitation is intended. For example, the first thread member 85 and the second thread member 94 may be joined to the flow path bodies 83 and 92 or the connection portions 84 and 93 by welding using heat, an adhesive or the like. Furthermore, for example, as illustrated in FIG. 27, the first thread member 85 and the second thread member 94 may be configured to be integrally formed with the sheet members 86 and 96, respectively. In the case of such a configuration, for example, the thread members 85 and 94 may be formed when the sheet members 86 and 96 are formed.

Furthermore, the first thread member 85 and the second thread member 94 may have a cross-section that is not a circular, but is irregular. Also, the first thread member 85 and the second thread member 94 may be formed of a material other than a resin material, as long as the material can elastically deform in accordance with the deformation of the cuff 71 and 73.

That is, the present invention is not limited to the embodiments described above, and various modifications can be made in an implementation stage within a range that does not depart from the gist of the present invention. Furthermore, each of the embodiments may be implemented in combination as appropriate to the extent possible, and in this case, combined effects can be obtained. Also, the embodiments described above include various stages of invention, and various inventions may be extracted by appropriately combining the described plurality of disclosed constituent elements.

REFERENCE SIGNS LIST

1 Blood pressure measurement device
3 Device body
4 Belt
5 Curler
5a Cover portion
5b Escape portion
5c Recess
5d Insert member
5e Screw hole
5f Hole portion
5f1 First hole portion
5f2 Second hole portion
5f3 Third hole portion
6 Cuff structure
7 Fluid circuit
7a First flow path
7b Second flow path
7c Third flow path
7d Fourth flow path
8 Power feeding unit
8a Wire portion
8b Power feeding terminal
8c Cover
11 Case
12 Display unit
13 Operation unit
14 Pump
15 Flow path portion
16 On-off valve
16A First on-off valve
16B Second on-off valve
16C Third on-off valve
16D Fourth on-off valve
17 Pressure sensor
17A First pressure sensor
17B Second pressure sensor
18 Power supply unit
19 Vibration motor
20 Control substrate
31 Outer case
31a Lug
31b Spring rod
32 Windshield
33 Base
34D1 First nozzle
34D2 Second nozzle
34D3 Third nozzle
35 Rear cover
35a First joining member
35b Second joining member
35c Hole portion
35d Hole portion
36 Sealing member
41 Button
42 Sensor
43 Touch panel
51 Substrate
52 Acceleration sensor
53 Communication unit
54 Storage unit
55 Control unit
56 Main CPU
57 Sub-CPU
61 First belt
61a Belt portion
61b Buckle
61c First hole portion
61d Second hole portion
61e Frame body
61f Prong
62 Second belt
62a Small hole
62b Third hole portion
71 pressing cuff
72 Back plate
72a Groove
73 Sensing cuff
74 Tensile cuff
75 Joining layer
81 Air bag (bag-like structure, first bag-like structure)
81a Weld portion
81b Bridge weld portion
82 Target join portion
83 Flow path body (first flow path body)
83a Weld portion
84 Connection portion (first connection portion)
85 First thread member
85a Thread 86 Sheet member
86a First sheet member
86b Second sheet member
86b1 Opening
86c Third sheet member
86c1 Opening
86d Fourth sheet member
86d1 Hole portion
91 Air bag (bag-like structure, second bag-like structure)
91a Weld portion
91b Junction margin
92 Flow path body (second flow path body)
92a Weld portion
93 Connection portion (second connection portion)
94 Second thread member
94a First thread
94b Second thread
96 Sheet member
96a Fifth sheet member
96b Sixth sheet member
96b1 Hole portion
101 Air bag (bag-like structure, third bag-like structure)
101a Weld portion
101b Bridge weld portion
102 Target join portion
102a Escape portion
103 Connection portion (third connection portion)
104 Cutout portion
106 Sheet member
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
106l1 Hole portion
111 First outer layer
112 First intermediate layer
113 Second intermediate layer
114 Second outer layer
200 Wrist
210 Artery

The invention claimed is:

1. A blood pressure measurement device comprising:
a device body internally including a pump and a flow path portion configured to supply a fluid from the pump to a secondary side;
a curler including a cover portion that curves to follow a circumferential direction of a wrist from a hand back side of the wrist along one side of the wrist to a region on a hand palm-side of the wrist where at least an artery resides, and the cover portion is configured to fix the device body to the hand back side of the wrist;
a belt provided on the device body, and configured to cover an outer circumferential surface of the curler;
a pressing cuff including a first bag-like structure, a first flow path body, and a first connection portion, the first bag-like structure formed by joining two sheet members formed of a resin material, fixed to an inner circumferential surface of the hand palm-side of the wrist of the curler, and configured to be inflated by a fluid supplied from the pump, the first flow path body integrally formed with the first bag-like structure by joining the two sheet members forming the first bag-like structure facing the curler, configured to fluidly connect the pump and the first bag-like structure, and including a leading end disposed on the wrist side of the cover portion, the first connection portion provided on the leading end of the first flow path body, and configured to be inserted in the cover portion and connected to the flow path portion;
a back plate fixed on the first bag-like structure on the wrist side of the pressing cuff, and curving to follow along the circumferential direction of the wrist;
a sensing cuff including a second bag-like structure, a second flow path body, and a second connection portion, the second bag-like structure formed by joining two sheet members, fixed to a main surface of the wrist side of the back plate, and configured to be inflated by fluid supplied from the pump, the second flow path body formed integrally with the second bag-like structure by joining the two sheet members forming the second bag-like structure, configured to fluidly connect the pump and the second bag-like structure, and including a leading end disposed on the wrist side of the cover portion, and the second connection portion provided on the leading end of the second flow path body, and configured to be inserted in the cover portion and connected to the flow path portion; and
a tensile cuff including a third bag-like structure and a third connection portion, the third bag-like structure formed by joining two sheet members, fixed to an inner circumferential surface of the hand back side of the wrist of the curler, and configured to be inflated by fluid supplied from the pump, and the third connection portion provided on the third bag-like structure facing the curler, and configured to be inserted in the cover portion and connected to the flow path portion, wherein
the pressing cuff includes a first thread member at least disposed in the first flow path body,
the sensing cuff includes a second thread member at least disposed in the second flow path body, and
the second thread member includes a first thread disposed in the second flow path body and a second thread that is formed to be longer than the first thread and is disposed in the second flow path body and the second bag-like structure.

2. The blood pressure measurement device according to claim 1, wherein the second thread member includes two of the first threads and one of the second thread.

3. The blood pressure measurement device according to claim 1, wherein the first thread member includes at least two threads disposed in the first flow path body.

4. The blood pressure measurement device according to claim 3, wherein
the first bag-like structure is joined in a quadrilateral frame shape smaller than an outer peripheral edge of the first bag-like structure and is fluidly continuous inside a joined join portion, and the first thread member is disposed from the first flow path body to the join portion.

5. The blood pressure measurement device according to claim 1, wherein the first thread member and the second thread member are set with a thread diameter of equal to or less than a sum of a thickness of the two sheet members.

6. The blood pressure measurement device according to claim 5, wherein the first connection portion and the second connection portion are nipples with an inner diameter that allows the first thread member and the second thread member to be inserted, and the first thread member and the second thread member are formed separate from the sheet member.

* * * * *